United States Patent
Hatada et al.

(10) Patent No.: US 6,486,113 B1
(45) Date of Patent: Nov. 26, 2002

(54) MUTANT α-AMYLASES

(75) Inventors: Yuji Hatada, Tochigi (JP); Kaori Ikawa, Tochigi (JP); Susumu Ito, Tochigi (JP); Kazuaki Igarashi, Tochigi (JP); Hiroshi Hagihara, Tochigi (JP); Yasuhiro Hayashi, Tochigi (JP); Hiroyuki Araki, Tochigi (JP); Katsuya Ozaki, Tochigi (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/381,687

(22) PCT Filed: Mar. 31, 1997

(86) PCT No.: PCT/JP98/01464

§ 371 (c)(1),
(2), (4) Date: Sep. 23, 1999

(87) PCT Pub. No.: WO98/44126

PCT Pub. Date: Oct. 8, 1998

(30) Foreign Application Priority Data

Mar. 31, 1997 (JP) .............................................. 9-080299

(51) Int. Cl.⁷ .......................... C11D 3/386; C12N 9/28; C12N 15/56
(52) U.S. Cl. ....................... 510/392; 510/300; 510/320; 510/530; 435/113; 435/440; 435/442; 435/187; 435/202; 435/204; 435/263
(58) Field of Search ................................ 510/300, 320, 510/392, 530; 435/113, 440, 442, 187, 202, 204, 263

(56) References Cited

U.S. PATENT DOCUMENTS 6,093,562 A * 7/2000 Bisgard-Frantzen et al. ..... 435/202

FOREIGN PATENT DOCUMENTS

| EP | WO 96/23873 | * 8/1996 | ............ C12N/9/28 |
|---|---|---|---|
| JP | 8506491 | 7/1996 | |
| JP | 8336392 | 12/1996 | |
| WO | WO 9418314 | 8/1994 | |
| WO | 94 26881 | 11/1994 | |
| WO | 95 26397 | 10/1995 | |
| WO | 96 23873 | 8/1996 | |
| WO | WO 9630481 | 10/1996 | |
| WO | 94 02597 | 2/1997 | |

OTHER PUBLICATIONS

The Journal of Biological Chemistry, vol. 264, No. 32, Issue of Nov. 15, pp. 18933–18938, 1989, Suzuki et al, Jul. 5, 1989.
A. Tsukamoto et al., Biochem. Biophys. Res. Commun., vol. 151 (1), Jan. 1988 pp. 25–31.
P.L. Jorgensen et al., FEMS Microbiology Letters, vol. 77 (2&3), Jan. 1991, pp. 271–275.
G.L. Gray et al., J. Bacteriol., vol. 166(2), May 1986, pp. 635–643.

* cited by examiner

Primary Examiner—Yogendra N. Gupta
Assistant Examiner—Brian P. Mruk
(74) Attorney, Agent, or Firm—Birch, Stewart, Kolasch & Birch, LLP

(57) ABSTRACT

The invention relates to a mutant α-amylase having an amino acid sequence obtained by making deletion or replacement by another arbitrary amino acid residue of at least a methionine residue at the 202-position or a position homologous thereto among amino acid residues set forth in SEQ ID NO:1, which constitute a liquefying alkaline α-amylase, a gene thereof, and a detergent composition comprising the mutant α-amylase. The mutant α-amylase has the optimum pH in an alkaline range, an excellent α-amylase activity, and high and lasting resistance to oxidizing agents, and is hence particularly useful as a component of detergent compositions containing a bleaching agent and an oxidizing agent.

10 Claims, 14 Drawing Sheets

```
KSMAP1378   1:HHNGTNGTMMQYFEWHLPNDGNHWNRLRDDAANLKSKGITAVWIPPAWKG  50
NCIB12512   1:HHNGTNGTMMQYFEWYLPNDGNHWNRLRDDAANLKSKGITAVWIPPAWKG  50
NCIB12289   1:HHNGTNGTMMQYFEWYLPNDGNHWNRLRDDAANLKSKGITAVWIPPAWKG  50
NCIB12513   1:HHNGTNGTMMQYFEWHLPNDGNHWNRLRDDASNLRNRGITAIWIPPAWKG  50
#707        1:HHNGTNGTMMQYFEWYLPNDGNHWNRLNSDASNLKSKGITAVWIPPAWKG  50
B.amylo     1:----VNGTLMQYFEWYTPNDGQHWKRLQNDAEHLSDIGITAVWIPPAYKG  46
B.stearo    1:-AAPFNGTMMQYFEWYLPDDGTLWTKVANEANNLSSLGITALWLPPAYKG  49
B.lichen    1:-AN-LNGTLMQYFEWYMPNDGQHWKRLQNDSAYLAEHGITAVWIPPAYKG  48
              ***  ******   **   *            *    **** * *** **

KSMAP1378   51:TSQNDVGYGAYDLYDLGEF-NQKGTVRTKYGTRSQLQGAVTSLKNNGIQV  99
NCIB12512   51:TSQNDVGYGAYDLYDLGEF-NQKGTVRTKYGTRNQLQAAVTSLKNNGIQV  99
NCIB12289   51:TSQNDVGYGAYDLYDLGEFNNQKGTVRTKYGTRNQLQAAVTSLKNNGIQV 100
NCIB12513   51:TSQNDVGYGAYDLYDLGEF-NQKGTVRTKYGTRSQLESAIHALKNNGVQV  99
#707        51:ASQNDVGYGAYDLYDLGEF-NQKGTVRTKYGTRSQLQAAVTSLKNNGIQV  99
B.amylo     47:LSQSDNGYGPYDLYDLGEF-QQKGTVRTKYGTKSELQDAIGSLHSRNVQV  95
B.stearo    50:TSRSDVGYGVYDLYDLGEF-NQKGTVRTKYGTKAQYLQAIQAAHAAGMQV  98
B.lichen    49:TSQADVGYGAYDLYDLGEF-HQKGTVRTKYGTKGELQSAIKSLHSRDINV  97
              *  *  *** ********* ***********              *    *

KSMAP1378  100:YGDVVMNHKGGADGTEMVNAVEVNRSNRNQEISGEYTIEAWTKFDFPGRG 149
NCIB12512  100:YGDVVMNHKGGADGTEIVNAVEVNRSNRNQETSGEYAIEAWTKFDFPGRG 149
NCIB12289  101:YGDVVMNHKGGADGTEIVNAVEVNRSNRNQETSGEYAIEAWTKFDFPGRG 150
NCIB12513  100:YGDVVMNHKGGADATENVLAVEVNPNNRNQEISGDYTIEAWTKFDFPGRG 149
#707       100:YGDVVMNHKGGADATEMVRAVEVNPNNRNQEVTGEYTIEAWTRFDFPGRG 149
B.amylo     96:YGDVVLNHKAGADATEDVTAVEVNPANRNQETSEEYQIKAWTDFRFPGRG 145
B.stearo    99:YADVVFDHKGGADGTEWVDAVEVNPSDRNQEISGTYQIQAWTKFDFNGRG 148
B.lichen    98:YGDVVINHKGGADATEDVTAVEVDPADRNRVISGEHRIKAWTHFHFPGRG 147
              * ***   **  *** **  * * ****          *  ***  * ***
```

FIG.1

(Continued from Fig.1)

```
KSMAP1378  150:NTHSNFKWRWYHFDGTDWDQSRQLQNKIYKFRGTGKAWDWEVDIENGNYD 199
NCIB12512  150:NNHSSFKWRWYHFDGTDWDQSRQLQNKIYKFRGTGKAWDWEVDTENGNYD 199
NCIB12289  151:NNHSSFKWRWYHFDGTDWDQSRQLQNKIYKFRGTGKAWDWEVDTENGNYD 200
NCIB12513  150:NTYSDFKWRWYHFDGVDWDQSRQFQNRIYKFRGDGKAWDWEVDSENGNYD 199
#707       150:NTHSSFKWRWYHFDGVDWDQSRRLNNRIYKFRGHGKAWDWEVDTENGNYD 199
B.amylo    146:NTYSDFKWHWYHFDGADWDESR-KISRIFKFRGEGKAWDWEVSSENGNYD 194
B.stearo   149:NTYSSFKWRWYHFDGVDWDESR-KLSRIYKFRGIGKAWDWEVDTENGNYD 197
B.lichen   148:STYSDFKWHWYHFDGTDWDESR-KLNRIYKF--QGKAWDWEVSNENGNYD 194
                * *** ****** *** **      * **     ********  ******

KSMAP1378  200:YLMYADIDMDHPEVINELRNWGVWYTNTLNLDGFRIDAVKHIKYSYTRDW 249
NCIB12512  200:YLMYADVDMDHPEVIHELRNWGVWYTNTLNLDGFRIDAVKHIKYSFTRDW 249
NCIB12289  201:YLMYADVDMDHPEVIHELRNWGVWYTNTLNLDGFRIDAVKHIKYSFTRDW 250
NCIB12513  200:YLMYADVDMDHPEVVNELRRWGEWYTNTLNLDGFRIDAVKHIKYSFTRDW 249
#707       200:YLMYADIDMDHPEVVNELRNWGVWYTNTLGLDGFRIDAVKHIKYSFTRDW 249
B.amylo    195:YLMYADVDYDHPDVVAETKKWGIWYANELSLDGFRIDAAKHIKFSFLRDW 244
B.stearo   198:YLMYADLDMDHPEVVTELKNWGKWYVNTTNIDGFRLDAVKHIKFSFFPDW 247
B.lichen   195:YLMYADIDYDHPDVAAEIKRWGTWYANELQLDGFRLDAVKHIKFSFLRDW 244
              ****** * *** *  *   ** ** *    **** ** **** *  **

KSMAP1378  250:LTHVRNTTGKPMFAVAEFWKNDLAAIENYLNKTSWNHSVFDVPLHYNLYN 299
NCIB12512  250:LTHVRNTTGKPMFAVAEFWKNDLGAIENYLNKTSWNHSVFDVPLHYNLYN 299
NCIB12289  251:LTHVRNTTGKPMFAVAEFWKNDLGAIENYLNKTSWNHSAFDVPLHYNLYN 300
NCIB12513  250:LTHVRNATGKEMFAVAEFWKNDLGALENYLNKTNWNHSVFDVPLHYNLYN 299
#707       250:INHVRSATGKNMFAVAEFWKNDLGAIENYLQKTNWNHSVFDVPLHYNLYN 299
B.amylo    245:VQAVRQATGKEMFTVAEYWQNNAGKLENYLNKTSFNQSVFDVPLHFNLQA 294
B.stearo   248:LSYVRSQTGKPLFTVGEYWSYDINKLHNYITKTNGTMSLFDAPLHNKFYT 297
B.lichen   245:VNHVREKTGKEMFTVAEYWQNDLGALENYLNKTNFNHSVFDVPLHYQFHA 294
               **  ***   * *  *      **  ** **    * ** ***
```

FIG.2

(Continued from Fig.2)

```
KSMAP1378  300:ASNSGGYFDMRNILNGSVVQKHPIHAVTFVDNHDSQPGEALESFVQSWFK 349
NCIB12512  300:ASNSGGYYDMRNILNGSVVQKHPTHAVTFVDNHDSQPGEALESFVQQWFK 349
NCIB12289  301:ASNSGGYYDMRNILNGSVVQKHPTHAVTFVDNHDSQPGEALESFVQQWFK 350
NCIB12513  300:ASNSGGNYDMAKLLNGTVVQKHPMHAVTFVDNHDSQPGESLESFVQEWFK 349
#707       300:ASKSGGNYDMRNIFNGTVVQRHPSHAVTFVDNHDSQPEEALESFVEEWFK 349
B.amylo    295:ASSQGGGYDMRRLLDGTVVSRHPEKAVTFVENHDTQPGQSLESTVQTWFK 344
B.stearo   298:ASKSGGAFDMSTLMNNTLMKDQPTLAVTFVDNHDTEPGQALQSWVDPWFK 347
B.lichen   295:ASTQGGGYDMRKLLNSTVVSKHPLKAVTFVDNHDTQPGQSLESTVQTWFK 344
               **  **  **         * *****  ***  *    * * *  ***

KSMAP1378  350:PLAYALILTREQGYPSVFYGDYY---GIPTHGVPSMKSKIDPLLQARQTY 396
NCIB12512  350:PLAYALVLTREQGYPSVFYGDYY---GIPTHGVPAMKSKIDPLLQARQTF 396
NCIB12289  351:PLAYALVLTREQGYPSVFYGDYY---GIPTHGVPAMKSKIDPLLQARQTF 397
NCIB12513  350:PLAYALILTREQGYPSVFYGDYY---GIPTHSVPAMKAKIDPILEARQNF 396
#707       350:PLAYALTLTREQGYPSVFYGDYY---GIPTHGVPAMRSKIDPILEARQKY 396
B.amylo    345:PLAYAFILTRESGYPQVFYGDMYGTKGTSPKEIPSLKDNIEPILKARKEY 394
B.stearo   348:PLAYAFILTRQEGYPCVFYGDYY---GIPQYNIPSLKSKIDPLLIARRDY 394
B.lichen   345:PLAYAFILTRESGYPQVFYGDMYGTKGDSQREIPALKHKIEPILKARKQY 394
               *****  ***  *** *****  *       *       * * *  **

KSMAP1378  397:AYGTQHDYFDHHDIIGWTREGDSSHPNSGLATIMSDGPGGNKWMYVGKHK 446
NCIB12512  397:AYGTQHDYFDHHDIIGWTREGNSSHPNSGLATIMSDGPGGNKWMYVGKNK 446
NCIB12289  398:AYGTQHDYFDHHDIIGWTREGNSSHPNDGLATIMSDGPGGNKWMYVGKNK 447
NCIB12513  397:AYGTQHDYFDHHNIIGWTREGNTTHPNSGLATIMSDGPGGEKWMYVGQNK 446
#707       397:AYGKQNDYLDHHNIIGWTREGNAHPNSGLATIMSDGAGGSKWMFVGRNK 446
B.amylo    395:AYGPQHDYIDHPDVIGWTREGDSSAAKSGLAALITDGPGGSKRMYAGLKN 444
B.stearo   395:AYGTQHDYLDHSDIIGWTREGVTEKPGSGLAALITDGPGGSKWMYVGKQH 444
B.lichen   395:AYGAQHDYFDHHDIVGWTREGDSSVANSGLAALITDGPGGAKRMYVGRQN 444
               *** * ** **    ******    ****   ** ** *  *
```

FIG.3

(Continued from Fig.3)

```
KSMAP1378  447:AGQVWRDITGNRSGTVTINADGWGNFTVNGGAVSVWVKQ----------- 485
NCIB12512  447:AGQVWRDITGNRTGTVTINADGWGNFSVNGGSVSVWVKQ----------- 485
NCIB12289  448:AGQVWRDITGNRTGTVTINADGWGNFSVNGGSVSVWVKQ----------- 486
NCIB12513  447:AGQVWHDITGNKPGTVTINADGWANFSVNGGSVSIWVKR----------- 485
#707       447:AGQVWSDITGNRTGTVTINADGWGNFSVNGGSVSIWVNK----------- 485
B.amylo    445:AGETWYDITGNRSDTVKIGSDGWGEFHVNDGSVSIYVQK----------- 483
B.stearo   445:AGKVFYDLTGNRSDTVTINSDGWGEFKVNGGSVSVWVPRKTTVSTIAWPI 494
B.lichen   445:AGETWHDITGNRSEPVVINSEGWGEFHVNGGSVSIYVQR----------- 483
               **   * ***   * *  **  *  **  * **  *

KSMAP1378  486:--------------------
NCIB12512  486:--------------------
NCIB12289  487:--------------------
NCIB12513  486:--------------------
#707       486:--------------------
B.amylo    484:--------------------
B.stearo   495:TTRPWTGEFVRWTEPRLVAWP                515
B.lichen   484:--------------------
```

MUTANT α-AMYLASES

This application is the national phase under 35 U.S.C. §371 of PCT International Application No. PCT/JP98/01464 which has an International filing date of Mar. 31, 1998 which designated the United States of America.

TECHNICAL FIELD

The present invention relates to mutant liquefying α-amylases which have the optimum pH in an alkaline range and excellent resistance to oxidizing agents and are particularly useful as enzymes for detergents comprising an oxidizing agent, and genes thereof.

BACKGROUND ART

Various enzymes are incorporated into detergents for the purpose of enhancing detergency, and it is considered to incorporate an α-amylase against, for example, starch smears. However, the α-amylase incorporated into a detergent must be an alkaline α-amylase, since the detergent comprises a surfactant, and the pH of a detergent solution is in an alkaline range.

By the way, detergents, in which an oxidation bleaching component is incorporated to expect not only detergency against dirt, but also a bleaching action, have been recently marketed. It is considered that the α-amylase is also incorporated into such an oxidation bleaching agent-containing detergent. However, the usual α-amylase is easy to inactivate in the presence of an oxidizing agent and has hence been unable to be incorporated into the oxidation bleaching agent-containing detergent.

Researches have been made to impart resistance to oxidizing agents to such an α-amylase. More specifically, WO 94/02597 has provided oxidizing agent-resistant mutant proteins by substituting a non-oxidizing amino acid, particularly, leucine (Leu), threonine (Thr) or glycine (Gly) for a methionine residue of an α-amylase derived from *B. licheniformis*. WO 94/18314 and WO 96/30481 have reported that when Met residues corresponding to the 197-position and 15-position among methionine residues in the same enzyme as described above are replaced by, in particular, Ala, Ile or Thr and Leu, Thr, Asp, Ser, Val or Ile, respectively, the resistance to oxidizing agents and heat stability of the enzyme are enhanced. However, these mutant α-amylases are all enzymes having the optimum pH in a neutral to acidic range, and there has thus been a demand for development of an alkaline α-amylase having a higher optimum pH for the purpose of using in detergents.

On the other hand, as a technique for imparting resistance to oxidizing agents to an alkaline α-amylase, WO 96/23873 has only reported oxidizing agent-resistant mutant α-amylases obtained by modifying SEQ ID NO:1 (NCIB 12512) encoding an α-amylase. According to WO 96/23873, taking into account the results of the α-amylase derived from *B. licheniformis* (WO 94/18314), and the like, it is described that when Met corresponding to the 202-position in FIG. 2 of NCIB 12512 is replaced by Leu, Phe, Ala, Thr, Val or Ser, the resultant α-amylase mutant becomes oxidizing agent-resistant to a treatment with 200 mM $H_2O_2$. It has however been reported that since its resistance to oxidation is insufficient, Arg at the 181-position and Gly at the 182-position are deleted in addition to this mutation (Suzuki et al., J. Biol. Chem., 264, 18933–18938, 1989) to more stabilize the mutant. However, the half-lives ($t_{1/2}$) of enzymatic activity of the mutant α-amylases obtained in such a manner are only in ranges of 10 to 20 minutes for the former and 10 to 30 minutes for the latter, and so they are not satisfactory as enzymes for incorporating into detergents for both resistance to oxidizing agents and lastingness thereof.

Accordingly, it is an object of the present invention to provide an α-amylase which has the optimum pH in an alkaline range and lasting and strong resistance to oxidizing agents, a gene thereof, and a detergent composition comprising such an α-amylase.

DISCLOSURE OF THE INVENTION

In view of the foregoing circumstances, the present inventors have paid attention to an enzyme produced by Bacillus sp. KSM-AP 1378 (WO 94/26881), which is a sort of liquefying alkaline α-amylase, and carried out various investigations. As a result, it has been found that when at least one methionine residue at the 202-position or a position homologous thereto in the amino acid sequence set forth in SEQ ID NO:1 is deleted or replaced by another arbitrary amino acid residue, the resultant α-amylase mutant comes to have strong and lasting resistance to oxidizing agents and has an excellent amylase activity in an alkaline pH range, thus leading to completion of the present invention.

According to the present invention, there is thus provided a mutant α-amylase having an amino acid sequence obtained by making deletion or replacement by another arbitrary amino acid residue of a methionine residue at the 202-position or a position homologous thereto in the amino acid sequence set forth in SEQ ID NO:1, which constitutes a liquefying alkaline α-amylase, or in an amino acid sequence having a homology of at least 95.2% to said amino acid sequence.

According to the present invention, there is also provided a gene encoding the mutant α-amylase.

According to the present invention, there is further provided a detergent composition comprising the mutant α-amylase.

BRIEF DESCRIPTION OF THE DRAWINGS

FIGS. 1 to 4 illustrate the homology between the amino acid sequence of a mature enzyme of α-amylase (KSM-AP 1378, KAM) produced by Bacillus sp. KSM-AP 1378 and the amino acid sequences of mature enzymes of α-amylases produced by other bacteria of the genus Bacillus. NCIB 12512 and NCIB 12513 are α-amylases described in WO 95/26397, NCIB 12289 is an α-amylase described in DK 94/0353 (DK 94-1271), #707 is an α-amylase produced by Bacillus. sp. #707, and BAA, BSA and BLA are α-amylases produced by *B. amyloliquefaciens, B. stearothermophilus* and *B. licheniformis*, respectively. A mark * given under the characters indicates that the homology exists on all the α-amylases.

FIGS. 8 and 9 diagrammatically illustrate the resistance to oxidation with $H_2O_2$ of various mutant α-amylases by amino acid replacement of methionine at the 202-position, which have been expressed with *Bacillus subtilis* and completely purified.

BEST MODE FOR CARRYING OUT THE INVENTION

Figure 5A:
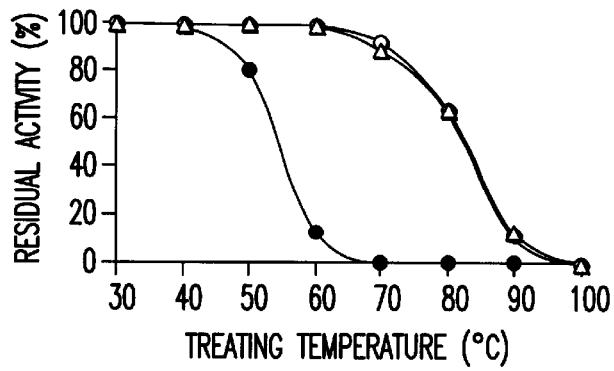
FIG. 5 diagrammatically illustrates the heat resistance and resistance to chelating agents (EDTA, EGTA and zeolite) of mutant α-amylases by amino acid deletion (ΔRG). ●: wild type, ○: ΔRG, and Δ: ΔRG/Met202Thr. A illustrates the heat resistance (treated at a varied temperature for 30 minutes under conditions of pH 8.5 in 50 mM Tris-HCl), and B to D illustrate the resistance to chelating agents (treated at 30° C. for 30 minutes in the presence of each of various chelating agents of a varied concentration under conditions of pH 8.5 in 50 mM Tris-HCl).
Figure 5B:
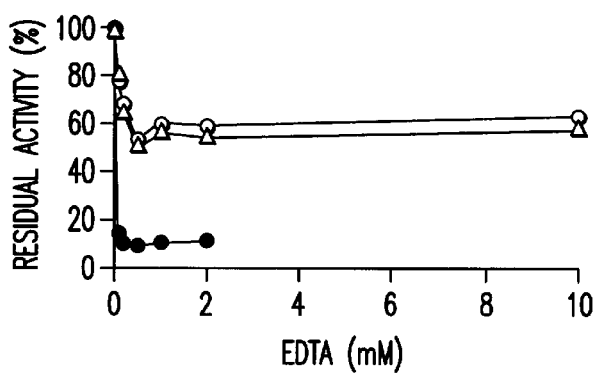
Figure 5C:
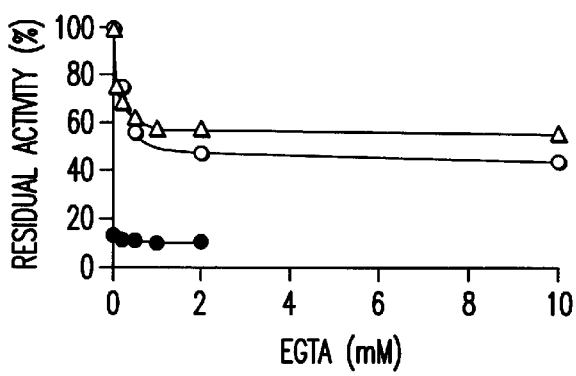
Figure 5D:
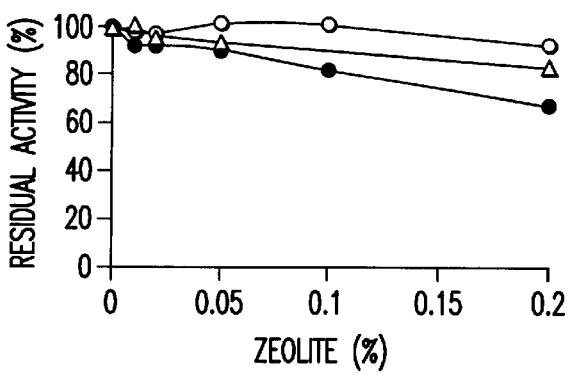
Figure 6:
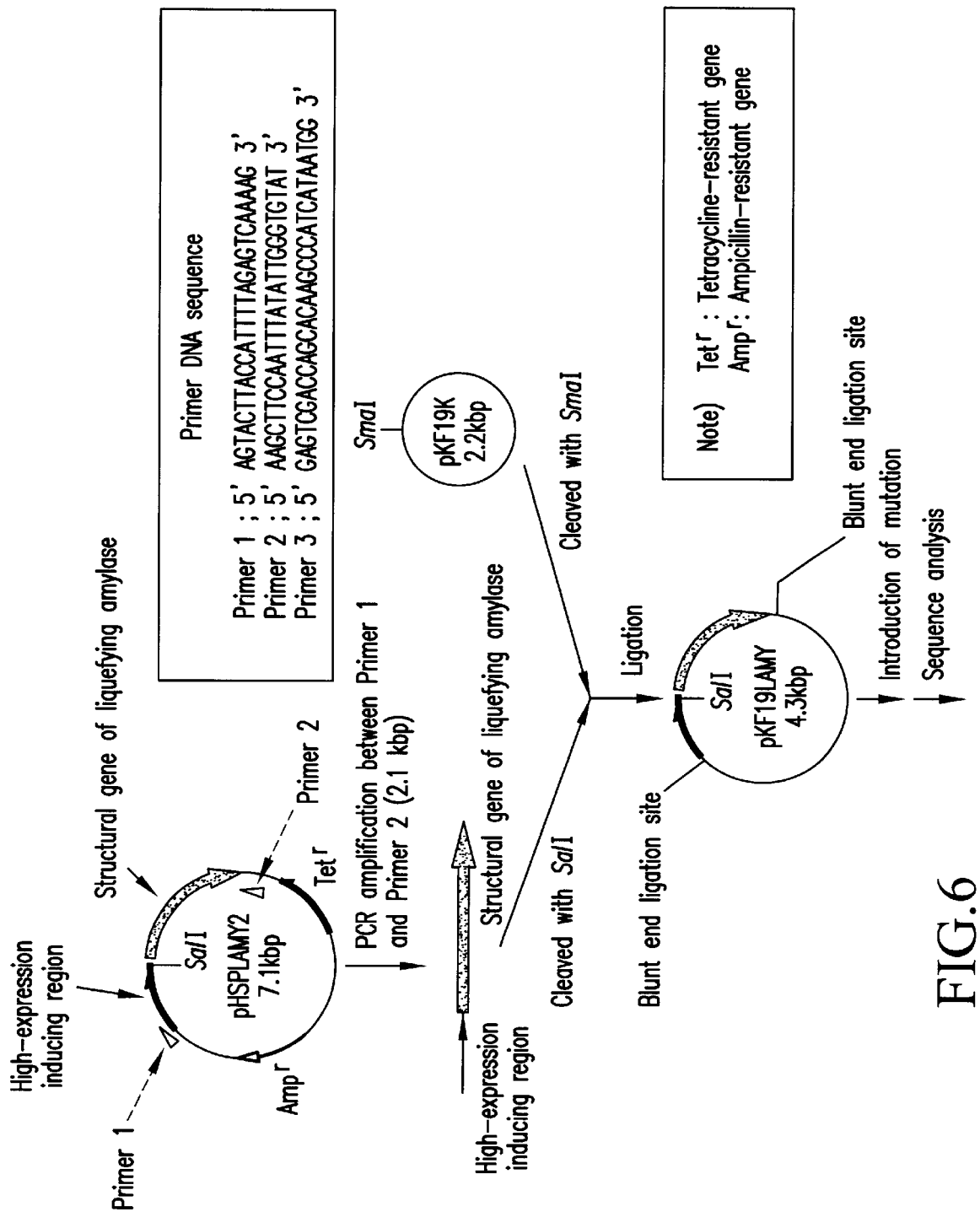
FIG. 6 schematically illustrates the introduction of a mutation into an α-amylase gene and the high extracellular production of a mutant α-amylase gene by *Bacillus subtilis*.

The mutant α-amylases according to the present invention are obtained by mutating a liquefying alkaline α-amylase. An example of the parental liquefying alkaline α-amylase includes a wild type liquefying alkaline α-amylase [deposited as Bucillus sp. KSM-AP 1378 (FERM BP-3048; original depositing date: Jul. 24, 1989) in National Institute of Bioscience and Human-Technology, Agency of Industrial Science and Technology (address: 1-3, Higashi 1 chome, Tsukuba-shi, Ibaraki-ken 305-0046, Japan) based on Budapest Treaty] previously reported by the present inventors and described in WO 94/26881.

The mutant α-amylases according to the present invention may be those having an amino acid sequence obtained by making deletion or replacement by another arbitrary amino acid residue of at least a methionine residue at the 202-position of the liquefying α-amylase having the amino acid sequence set forth in SEQ ID NO:1. No particular limitation is imposed on another arbitrary amino acid residue used herein so far as it is a non-oxidizing amino acid residue, and for example, Thr, Ile, Leu, Ala, Val or Ser is preferred.

The mutant α-amylases according to the present invention obtained by making deletion or replacement by another amino acid residue of only a methionine residue at the 202-position in SEQ ID NO:1 each have a half-life ($t_{1/2}$) of activity amounted to several hours ($t_{1/2}$ of wild type α-amylase: about 10 to 20 minutes) even in the presence of $H_2O_2$ at a concentration as high as 500 mM and are markedly excellent in resistance to oxidizing agents and lastingness thereof compared with the mutant α-amylases described in WO 96/23873.

As described above, the mutants according to the present invention obtained by the replacement of Met at the 202-position by a non-oxidizing amino acid have a high resistance to $H_2O_2$, which is a strong oxidizing agent, even at a high concentration. The very surprising fact is that the amino acid sequence of the parental α-amylase used in the present invention has a homology of 95.1% with that of NCIB 12512 (SEQ ID NO:1) in WO 96/23873. Only 24 amino acids among 485 amino acids in total differ in amino acid sequence. In the I, II, III and IV regions well conserved in the α-amylase family, there is no difference. Since the sequence of the parental α-amylase according to the present invention has homologies of 86.6%, 94.7%, 86.4%, 66.7%, 68.6% and 68.9%, respectively, with those of NCIB 12513

(WO 95/26397), NCIB 12289 (DK 94-1271), Bacillus. sp. #707, B. amyloliquefaciens, B. stearothermophilus and B. licheniformis, the amino acid homology of the parental α-amylase used in the present invention is therefore preferably at least 95.2% to the amino acid sequence of SEQ ID NO:1.

In the case of the α-amylase of SEQ ID NO:1, even if other methionine residues than the methionine residue at the 202-position, for example, the methionine residues at the 9-, 10-, 105-, 116-, 208-, 261-, 309-, 382-, 430- and 440- positions, are deleted or replaced by another amino acid residue, no high resistance to oxidizing agents can be achieved. Therefore, these methionine residues do not need to be particularly modified. When the methionine residue at the 202-position is replaced by another amino acid, it is preferred to substitute Thr, Ile, Leu, Ala, Val or Ser for it.

An α-amylase having an amino acid sequence obtained by making further deletion of an arginine residue at the 181-position and a glycine residue at the 182-position in SEQ ID NO:1 is particularly preferred because it also has heat resistance (resistance to chelating agents) in addition to the resistance to oxidizing agents.

Since the amino acid sequence of the wild type α-amylase used in the present invention originally has a useful nature from the viewpoint of protein engineering compared with industrial α-amylases such as B. licheniformis, B. amyloliquefaciens and B. stearothermophilus, and resistance to oxidation and heat resistance (resistance to chelating agents) are imparted thereto by leaps and bounds by only creating an Met202X (X: an arbitrary amino acid) and a mutant enzyme by RG deletion, mutant α-amylases having an industrially very useful nature can be obtained by applying these mutations either singly or in combination.

The mutant α-amylases according to the present invention are produced by, for example, introducing a site-specific mutation into a DNA encoding the amino acid sequence of SEQ ID NO:1 to give a gene encoding an mutant α-amylase and a vector plasmid containing this gene, then giving a transformant by transformation of a host using this plasmid, or chromosomal homologous recombination, and culturing the transformant.

First of all, the DNA encoding the liquefying alkaline α-amylase having the amino acid sequence of SEQ ID NO:1 can be obtained in accordance with, for example, the process described in Japanese Patent Application Laid-Open No. 336392/1996.

As a method for making the site-specific mutation, any method may be adopted so far as it is a method commonly performed. However, the mutation can be performed, for example, by using a Transformer Site-Directed Mutagenesis Kit produced by Clonetech Co., a Site-Directed Mutagenesis System Mutan-Super Express Km Kit produced by TaKaRa Co., or the like.

The screening of a clone which produces an oxidizing agent-resistant α-amylase mutant is conducted by culturing the transformant on a soluble starch-containing medium.

General methods adopted in the practice of the process according to the present invention will hereinafter be described.
[Extraction Method of Chromosome DNA]
The isolation of a chromosome from the above-described strain may be performed in accordance with a method known per se in the art, for example, the method by Saito & Miura (Biochim. Biophys. Acta, 72, 619–629, 1963).
[Method for Introducing Plasmid DNA into *Escherichia coli*]

The introduction of a plasmid DNA into *Escherichia coli* was performed by using a competent cell (TaKaRa Co.). Incidentally, a 0.6% starch azure (product of Sigma Co.) was added to a solid LB medium for the purpose of selecting an amylase-active transformant.
[Preparation Method of Cell-free Extract and Culture Supernatant]
*Escherichia coli* containing the intended plasmid DNA was subjected to shaking culture for 15 to 24 hours in a liquid LB medium (50 ml) containing tetracycline (15 μg/ml). The culture medium was centrifuged, and the resultant cell pellets were suspended in 5 ml of 50 mM Tris-HCl (pH: 8.0). The cell suspension was subjected to cell disruption by means of an ultrasonication apparatus. The disrupted cell suspension was centrifuged, and the resultant supernatant was taken out as a cell-free extract. On the other hand, the culture medium after the culture was centrifuged, and the resultant supernatant was used in enzyme assay.
[Preparation Method of Plasmid DNA]
The preparation of a plasmid DNA from the recombinant *Escherichia coli* can be performed by using the method by Maniatis et al. (Moleculer Cloning, A Laboratory Manual, Cold Spring Harbor Laboratory, N.Y., U.S.A., 1982) in accordance with a method known per se in the art.
[Determination of Base Sequence]
The determination of a base sequence can be performed by using the chemical modification method by Maxam-Gilbert (Methods Enzymol., 65,499–559, 1980) or the dideoxynucleotide chain termination method (Sanger et al., Proc. Natl. Acad. Sci., U.S.A., 74,5463–5467, 1977; Smith et al., Nature, London, 321,674–679, 1986).
[Method for Introducing Site-specific Mutation]
The introduction of a site-specific mutation can be performed by using a Transformer Site-Directed Mutagenesis Kit (2nd version) or a Site-Directed Mutagenesis System Mutan-Super Express Km Kit produced by TaKaRa Co. in accordance with the protocol of Clontech Co.
[Determination of Amylase Activity]
The amylase activity of each enzyme was determined by the 3,5-dinitrosalicylic acid method (DNS method). After a reaction was conducted at 40° C. for 15 minutes in a reaction mixture with soluble starch contained in a 50 mM Tris-HCl buffer (pH: 8.5), reducing sugar formed was determined by the DNS method. With respect to the enzymatic activity, the amount of the enzyme, which forms reducing sugar corresponding to 1 μmol of glucose for 1 minute, was defined as 1 unit.
[Determination of Protein Content]
The protein content was determined by means of a Protein Assay Kit produced by Bio-Rad Laboratories making use of bovine serum albumin as a standard.
[Assay of Resistance to Oxidation with $H_2O_2$]
(1) The amylase activity of a sample was first determined in advance, and the sample was then diluted with a proper buffer, for example, a 50 mM Tris-HCl (pH: 8.5 or 8.9) to an amylase enzyme concentration about a half as much as an amylase enzyme concentration that can be directly determined without dilution.
(2) Each 5 μl of a catalase (Behringer Mannheim GmbH, 20 mg/ml) was poured into test tubes (sample×5 tubes).
(3) A 30% aqueous hydrogen peroxide solution (Wako Pure Chemical Industries, Ltd.) was diluted to a final concentration of 200 mM or 500 mM with a buffer.
(4) Test tubes (sample×2 tubes) equipped with a threaded closure were provided, a mixed solution of the diluted enzyme solution (1 ml) prepared in the step (1) and a buffer (1 ml) was poured into one tube of them, and the diluted enzyme solution (3 ml) prepared in the step (1) was poured into the other tube. The tubes were incubated at 30° C. or 40° C.

(5) The aqueous hydrogen peroxide solution (3 ml) prepared in the step (3) was quickly added to a test tube containing the diluted enzyme solution (3 ml) and incubated at 4° C., and the contents were thoroughly mixed. Each 700 µl of the reaction mixture was sampled after allowed to stand for prescribed periods of time, and poured into the catalase-containing test tube provided in the step (2) to terminate the oxidation. After the pouring, the tube was kept into an ice bath until the activity was determined. At the same time, the hydrogen peroxide-free samples incubated at 30° C. or 40° C. in the step (4) were also transferred to the ice bath.

(6) The residual amylase activities of the respective samples were determined by the DNS method to find their resistance to the oxidizing agent (hydrogen peroxide). Incidentally, in order to confirm the fact that the amylase activity is not deteriorated by only the incubation at 30° C. or 40° C., the amylase activities of the hydrogen peroxide-free samples placed into the ice bath in the step (5) and the diluted enzyme solution prepared in the step (1) were also determined at the same time.

The thus-obtained mutant α-amylases according to the present invention have extremely high and lasting resistance to oxidizing agents and are hence useful as a component of detergents containing an oxidizing agent and a bleaching agent, compositions for liquefication and saccharification of starch, and the like.

The detergent composition according to the present invention may comprise one or more enzymes selected from debranching enzymes (pullulanase, isoamylase, neopullulanase, etc.), α-glycosidases, glucoamylases, proteases, cellulases, lipases, pectinases, protopectinases, pectic acid lyases, peroxidases, laccases and catalases in addition to the above-described mutant α-amylases.

Further, surfactants such as anionic surfactants, amphoteric surfactants, nonionic surfactants and cationic surfactants; divalent metal ion sequesrants (chelating agents), alkalizing agents, inorganic salts, resoiling preventives, chlorine scavengers, reducing agents, bleaching agents, fluorescent dye solubilizers, perfume bases, caking preventives, enzyme activators, antioxidants, preservatives, coloring matter, bluing agents, bleaching activators, enzyme stabilizers, phase adjusters, etc., which are commonly incorporated into the classical detergents, may be incorporated.

The form of the detergent composition may be suitably selected as necessary for the end application intended, and the detergent composition may be provided in the form of, for example, liquid, powder or granules. The detergent composition according to the present invention can be used as a laundry detergent, bleaching detergent, detergent for automatic dish washer, drain cleaner, artificial tooth cleaner or the like. In particular, it can preferably used as a laundry detergent, bleaching detergent or detergent for automatic dish washer.

EXAMPLES

The present invention will hereinafter be described in more detail by the following Examples. However, the present invention is not limited in any way to these examples.

Example 1

(1) Introduction of Mutation into Liquefying Alkaline α-amylase Gene

A Site-Directed Mutagenesis System Mutan-Super Express Km Kit produced by TaKaRa Co. and a primer for introduction of a mutation, which can substitute a codon of another amino acid for a codon of Met at the 202-position, were used to make a mutation against the codon encoding the Met at the 202-position.

For example, when a 24 mer of 5'TACCTT CTGTATGCAGACATTGAT3' is used as the primer for introduction of mutation, a sequence of CTG located at the 7th to 9th positions in this sequence is a sequence encoding Leu and corresponds to a position of an ATG sequence encoding Met at the 202-position in a template sequence annealed, so that a methionine residue is replaced by a leucine residue by the replacement in sequence from ATG to CTG (hereinafter abbreviated as Met202Leu).

In the present invention, the introduction of mutation into the 202-position of Met gives 5 oxidation-resistant α-amylase mutant in addition to Met202Leu. Primers used for introducing such mutations are shown below.

| 5'TACCTTXXX*TATGCAGACATTGAT3' | |
| --- | --- |
| Met202Ala | GCA |
| Met202Ile | ATC |
| Met202Ser | TCA |
| Met202Thr | ACA |
| Met202Val | GTG |
| (Met202Cys | TGC |

(*: XXX are 3 bases replaced)

A specific method for introducing a mutation will be described below.

① Introduction of α-amylase Gene into Plasmid Vector pKF19K for Introduction of Mutation A 2.1 kb fragment containing a liquefying α-amylase structural gene was amplified from a high-expression promoter region on a plasmid pHSPLAMY2 for high production of α-amylase by PCR to insert it into an Sma I site of a plasmid pKF19K (named it pKF19LAMY).

② PCR for Introduction of Mutation

The following reaction mixture was prepared in a reaction tube (0.5 ml). The composition of the reaction mixture: template DNA (pKF19LAMY) 10 ng, selection primer 5 pmol, phosphorylated primer for introduction of mutation 5 pmol, 10×LA PCR buffer II 5 µl, dNTP mixture (each 2.5 mM) 8 µl and TaKaRa LA TAG 0.5 µl (total 50 µl). PCR reaction was performed under conditions as described below: A cycle of dissociation at 94° C. for 1 minute, annealing at 55° C. for 1 minute and elongation at 72° C. for 3 minutes was repeated 25 times, and then 10 minutes at 4° C. An amplified DNA was purified with a PCR fragment purification kit (Behringer Mannheim GmbH) and used in transformation.

③ Introduction into *Escherichia coli* MV1184 Strain and Confirmation of Mutation

*Escherichia coli* MV1184 competent cells (TaKaRa Co.) were used to introduce the PCR product into an *Escherichia coli* MV1184 strain (araΔ(lac-proAB)rpsLthi(ø80 lac ZΔM15) Δ(srl-recA)306::Tn10(tet$^r$)F' [traD36proAB$^+$lacI$^q$ lacZΔM15]) by a usual competent cell method. A plasmid DNA was prepared from several transformant colonies grown on an LB agar medium (Bactotryptone 1%, yeast extract 0.5%, sodium chloride 1%, agar 1.5%) containing kanamycin (50 µg/ml), and sequence analysis was conducted to confirm the mutation.

(2) Screening of Oxidizing Agent-resistant α-amylase Mutant

Each transformant culture medium was first centrifuged at 12,000 rpm for 15 minutes for the purpose of obtaining a mutant α-amylase in accordance with the above-described process, thereby recovering a culture supernatant. Aqueous hydrogen peroxide was added to each culture supernatant so as to give a final concentration of 2%. After the mixture was allowed to stand at 30° C. for 30 minutes, the residual amylase activity of the culture supernatant was determined. At the same time, the amylase activity of each hydrogen peroxide-free culture supernatant treated under the same conditions was also determined.

The residual activity after treated with hydrogen peroxide was compared with that of a wild type enzyme to obtain 18 mutants that were judged to have high resistance to the oxidizing agent (retaining 85 to 100% activity). Respective plastids were prepared from 11 transformants selected to conduct their sequence analyses. As a result, it was clarified that the amino acid at the 202-position was replaced from a methionine residue to a threonine residue (2 clones), a serine residue (2 clones), a valine residue (2 clones), a leucine residue (1 clone), a isoleucine residue (3 clones) or an alanine residue (1 clone). These mutants concurred in substituted amino acids with the oxidation-resistance mutant α-amylases obtained by the site-specific mutation. These mutant α-amylase genes or proteins were named Met202Thr, Met202Ile, Met202Leu, Met202Ala, Met202Val and Met202Ser. With respect to Met202Cys, when the enzyme was completely purified and mixed with water, the mixture became opaque and the enzyme precipitated. It is probable that the enzyme forms a disulfide bond between its molecules to become insoluble.

(3) The mutant α-amylases (supernatants) obtained by centrifuging culture media expressed with the *Escherichia coli* were precipitated with 60% ammonium sulfate. The precipitates were separately dialyzed, and each unadsorbed portion on a DEAE-Toyoperl 650S column was then concentrated to obtain a partial purified preparation of the mutant enzymes. The resistance to the oxidizing agent ($H_2O_2$) of the thus-obtained preparations was confirmed. As a result, the mutant α-amylases other than Met202Cys had a residual activity of at least 75% even after treated at 30° C. for 30 minutes in the presence of 1 to 3% $H_2O_2$ in a 50 mM Tris-HCl buffer (pH: 8.5).

(4) Similarly, the following primers were suitably used to replace other methionine residues, i.e., Met residues at the 9-, 105-, 116-, 382- and 430-positions, by respective proper amino acids.

Met9Leu: 5'ACGAATGGGACCCTGATGCAGTATTTT3'

Met105Ile: 5'GGGGATGTCGTGATCAATCATAAAGGT3'

Met116Asp: 5'GACGGGACAGAGGACGTAAATGCGGTG3'

Met382Leu: 5'GGTGTTCCTTCGCTGAAATCTAAAATT3'

Met430Ile: 5'CTTGCAACTATTATCTCCGATGGGCCA3'

With respect to these amino acid substitutions, when an amino acid was selected at random, it was considered that a normal protein structure cannot be taken due to steric structural hindrance, or that if taken, activity expression is inhibited, and so amino acids corresponding to the amino acid sequence of the α-amylase derived from *B. licheniformis* were selected (see FIGS. 1 to 6). According to Japanese Patent Application (KOHYO) No. 500243/1995 (though PCT route), it is described that mutants obtained by replacing one or both of methionine residues at the 202-position and 208-position in the liquefying α-amylase derived from *B. stearothermophilus* are stabilized, and in WO 96/23878, the same description is given even in the α-amylase derived from NCIB 2512. Therefore, 5'GCAGACATTGATATGATCATCCAGAA3' was synthesized as a primer for mutation to prepare Met208Tyr.

By the way, if the known report by Suzuki et al. (J. Biol. Chem., 264, 18933–18933, 1989), i.e., specific deletion of 2 amino acids, arginine and glycine is reproduced even in the α-amylase in the present invention, it is expected that not only resistance to oxidizing agents, but also heat stability is enhanced. Therefore, arginine at the 181-position and glycine at the 182-position of a gene of the wild type α-amylase and a gene of an α-amylase having Met202Thr mutation, said positions corresponding to the report by Suzuki et al., are deleted by using the following primer for introduction of a mutation, thereby creating 2 mutant α-amylase by deletion (hereinafter abbreviated as ΔRG and ΔRG/Met202Thr, respectively).

ΔRG: 5'AAAATATATAAATTC(AGA)(GGT)ACCGGAAAGGCATGGGACTGG3' (bases in parentheses indicate deleted bases)

The above-described mutant plasmids were expressed in *Bacillus subtilis* cells and then mutant α-amylases produced were purified to determine resistance to oxidation with $H_2O_2$. The results are shown in Table 1.

TABLE 1

| | Residual activity (%)* Treating concentration of $H_2O_2$ (%) | | | |
|---|---|---|---|---|
| Mutant amylase | 0 | 1.0 | 2.0 | 3.0 |
| Wild type | 100 | 18.8 | 4.9 | 3.0 |
| Met9Leu | 100 | 15.6 | 4.5 | 3.4 |
| Met105Leu | 100 | 14.8 | 5.2 | 4.1 |
| Met116Asp | 100 | 20.1 | 5.3 | 4.0 |
| Met382Leu | 100 | 19.7 | 4.9 | 3.9 |
| Met430Leu | 100 | 18.5 | 5.6 | 5.2 |
| Met208Tyr | 100 | 19.1 | 5.2 | 4.3 |
| Met202Leu (control) | 100 | 90 | 86 | 78 |
| ΔRG (control) | 100 | 19 | 4.4 | 2.9 |
| ΔRG/Met202Thr | 100 | 95 | 93 | 92 |

*Pretreated with $H_2O_2$ at 30° C. for 30 minutes in 50 mM Tris-HCl (pH: 8.5). In each sample, expressed in terms of a relative value regarding the activity of $H_2O_2$-free system as 100%.

As apparent from Table 1, it is understood that all the Met9Leu, Met105Ile, Met116Asp, Met382Leu, Met430Ile, Met208Tyr and ΔRG only have resistance to oxidation equivalent to the wild type enzyme, namely, have no resistance to oxidizing agents. On the other hand, ΔRG/Met202Thr obtained by introducing the ΔRG mutation into Met202Thr exhibiting high resistance to oxidizing agents exhibited high resistance to oxidizing agents like Met202Leu as a control. In addition, it is apparent from FIG. 5 that this enzyme and ΔRG are highly improved in heat resistance and resistance to chelating agents (EDTA, EGTA and zeolite) compared with the wild type enzyme.

Figure 7:
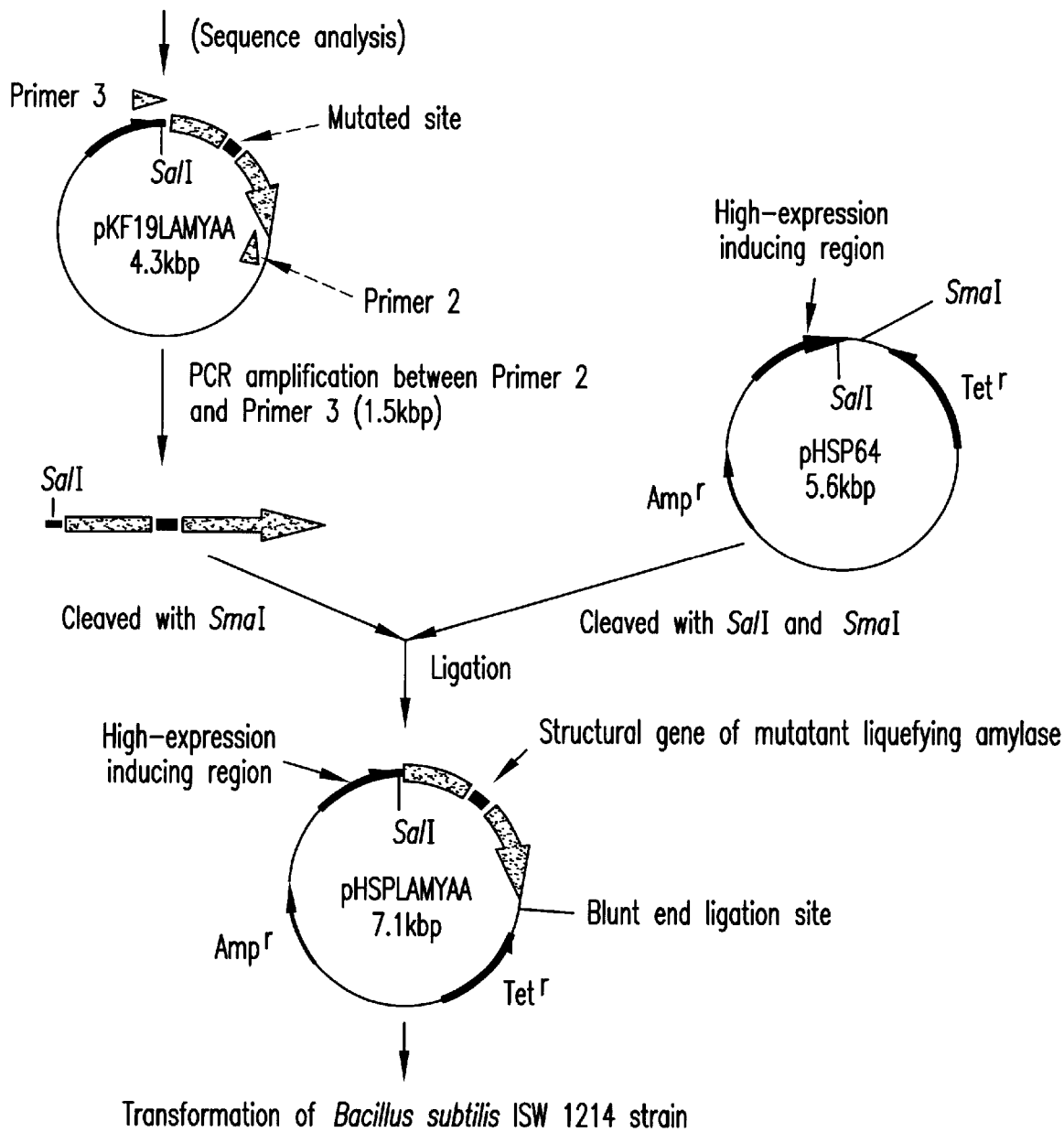
FIG. 7 schematically illustrates the introduction of a mutation into an α-amylase gene and the high extracellular production of a mutant α-amylase gene by *Bacillus subtilis* (continued from FIG. 6). A portion of "Sequence analysis" in parentheses overlaps FIG. 6.
Figure 8A:
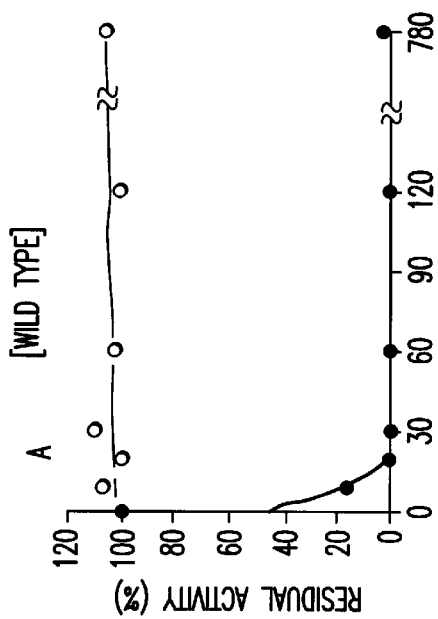
FIGS. 8A and 8C show residual activities after treated with 2% $H_2O_2$ for prescribed periods of time in a 50 mM Tris-HCl buffer (pH: 8.5; in the presence of 0.1 mM $CaCl_2$) under conditions according to the present invention (KAO method), respectively.
Figure 8B:
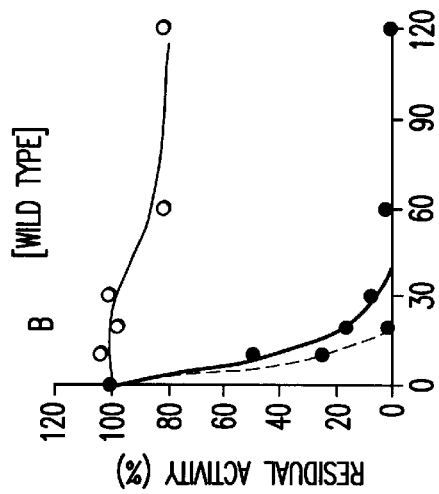
FIGS. 8B and 8D show residual activities after treated with 200 mM $H_2O_2$ for prescribed periods of time in a Britton-Robinson buffer (pH: 9.0; in the presence of 0.1 mM $CaCl_2$) under conditions described in WO 96/23873 (W method) for both wildtype and the Met202Ala mutant, respectively.
Figure 8C:
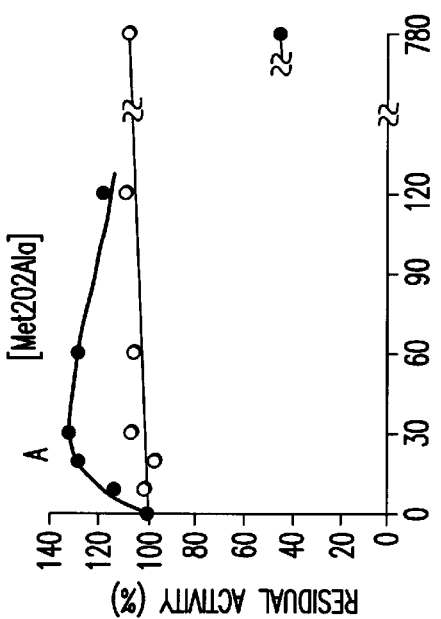
Figure 8D:
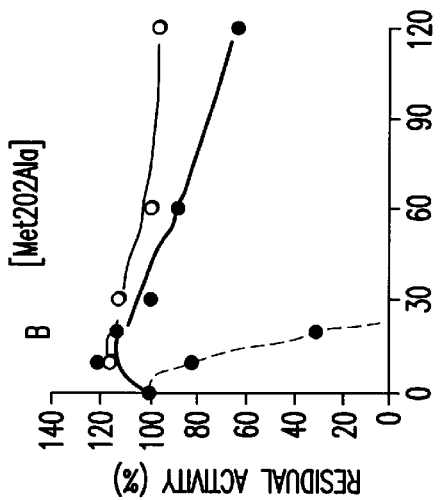
Figure 9A:
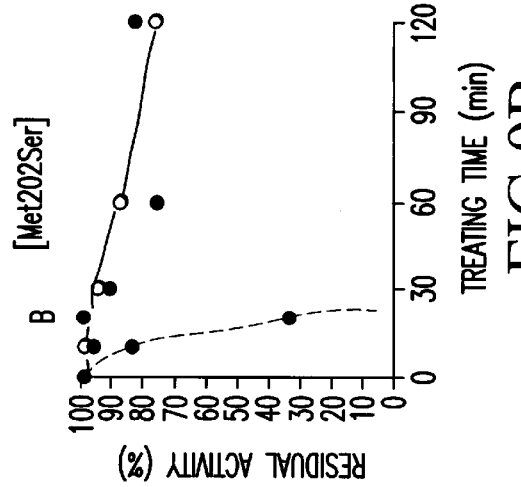
FIGS. 9A and 9C show residual activities after being treated with 2% $H_2O_2$ for prescribed periods of time in a 50 mM Tris-HCl buffer (pH: 8.5; in the presence of 0.1 mM $caCl_2$) for both Met202Ser mutant and Met202Val mutant under conditions according to the present invention (KAO method), respectively.
Figure 9B:
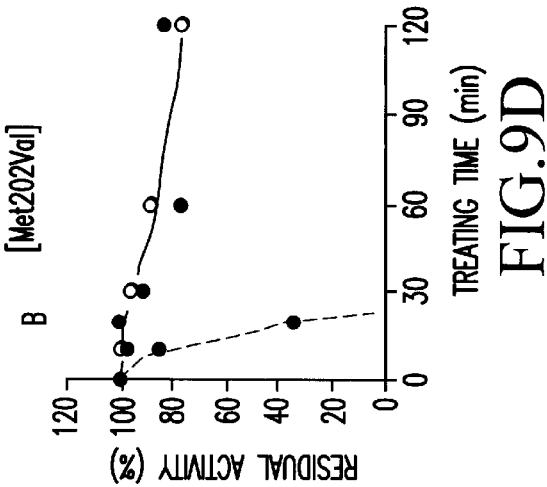
FIGS. 9B and 9D show residual activities after being treated with 200 mM $H_2O_2$ for prescribed periods of time in a Britton-Robinson buffer (pH: 9.0; in the presence of 0.1 mM $CaCl_2$) for both the Met202Ser mutant and the Met202Val mutant under conditions described in WO 96/23873 (W method), respectively. For the sake of comparison, the result of the α-amylase derived from NCIB (12215, SEQ ID NO:1 in WO 96/23873) is added in FIGS. 8B and 8D (indicated by a broken line in the drawing). ○: pretreated in the absence of $H_2O_2$ (control), and ●: pretreated with $H_2O_2$ of the prescribed concentration.
Figure 9C:
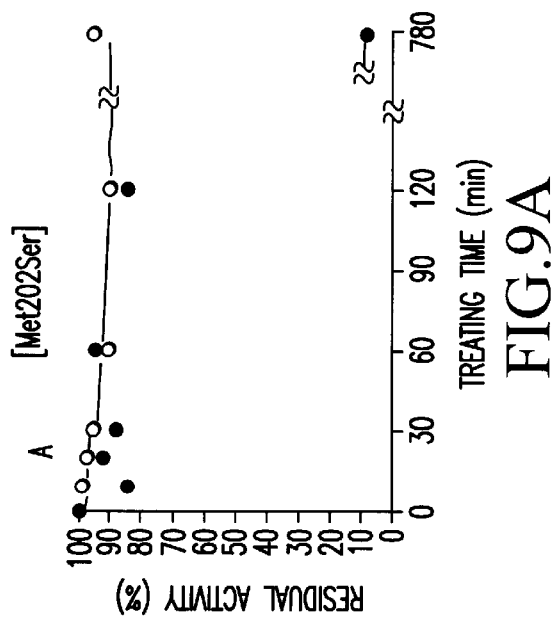
Figure 9D:
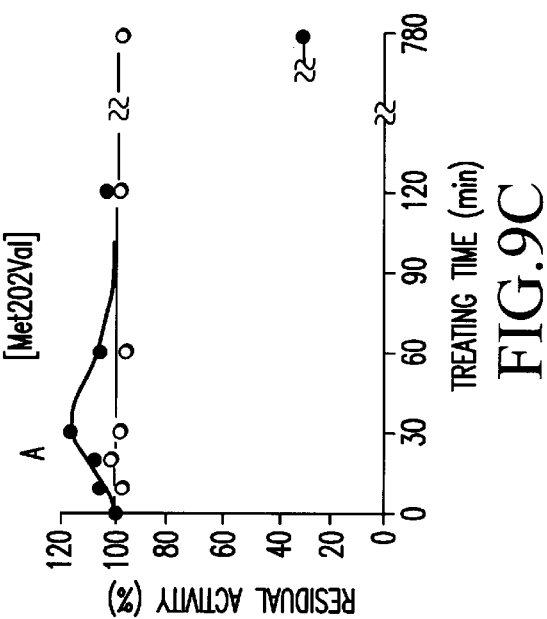
Figure 10A:
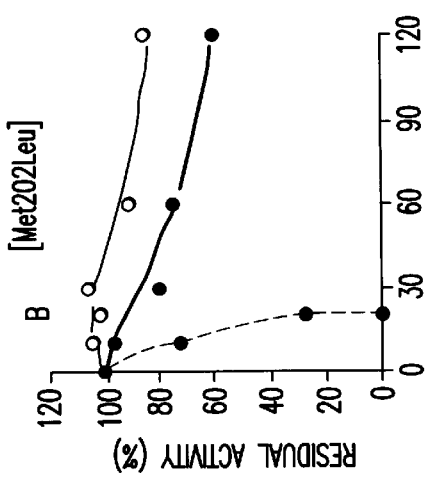
FIGS. 10A and 10C show residual activities after being treated with 500 mM $H_2O_2$ for prescribed periods of time in a 50 mM Tris-HCl buffer (pH: 8.9; in the presence of 0.1 mM $CaCl_2$ for mutants Met202Leu and the Met202Ile mutant under conditions according to the present invention (KAO method), and FIGS. 10B and 10D show residual activities after being treated with 200 mM $H_2O_2$ for prescribed periods of time in a Britton-Robinson buffer (pH: 9.0; in the presence of 0.1 mM $CaCl_2$) for mutants Met202Leu and Met202Ile under conditions described in WO 96/23873 (W method) respectively.
Figure 10C:
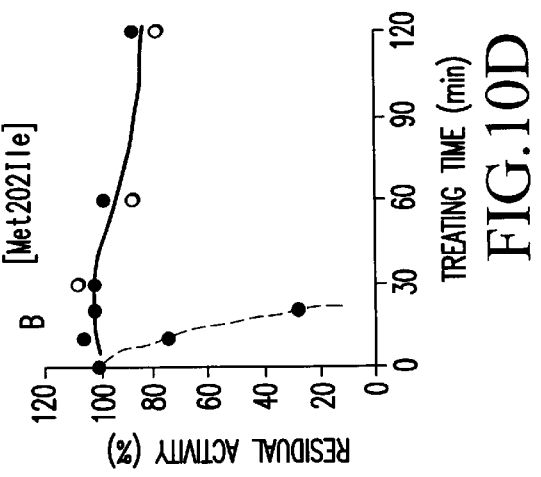
Figure 10B:
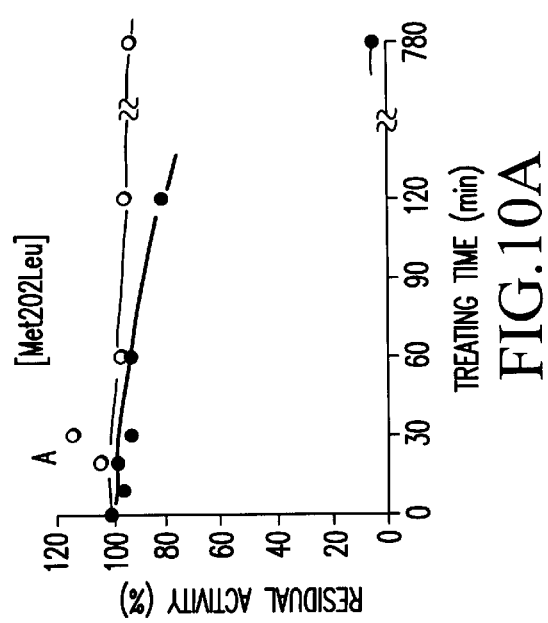
FIGS. 10 and 11 diagrammatically illustrate the resistance to oxidation with $H_2O_2$ of various mutant α-amylases by amino acid replacement of methionine at the 202-position, which have been expressed with *Bacillus subtilis* and completely purified.
Figure 10D:
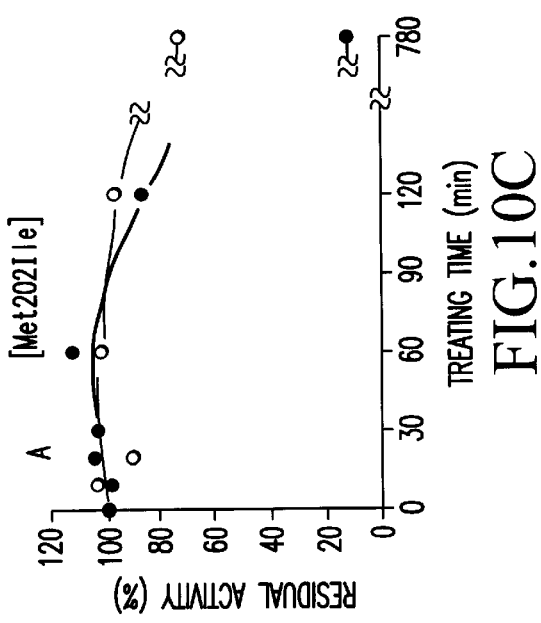
Figure 11A:
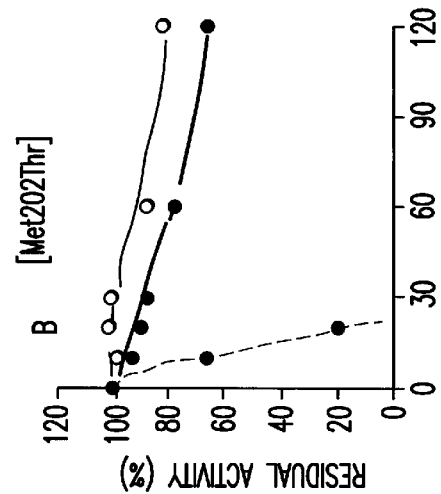
FIGS. 11A and 11C show residual activities after being treated with 500 mM $H_2O_2$ for prescribed periods of time in a 50 mM Tris-HCl buffer (pH: 8.9; in the presence of 0.1 mM $CaCl_2$ for mutants Met202Thr and ΔRG under conditions according to the present invention (KAO method), and FIGS. 11B and 11D show residual activities after being treated with 200 mM $H_2O_2$ for prescribed periods of time in a Britton-Robinson buffer (pH: 9.0; in the presence of 0.1 mM $CaCl_2$) for mutants Met202Thr and ΔRG under conditions described in Wo 96/23873(W method) respectively. For the sake of comparison, the result of the α-amylase derived from NCIB (12215, SEQ ID NO:1 in WO 96/23873) is added in FIGS. 10B, 10D and 11B (indicated by a broken line in the drawing). ○: pretreated in the absence of $H_2O_2$ (control), and ●: pretreated with $H_2O_2$ of the prescribed concentration.
Figure 11B:
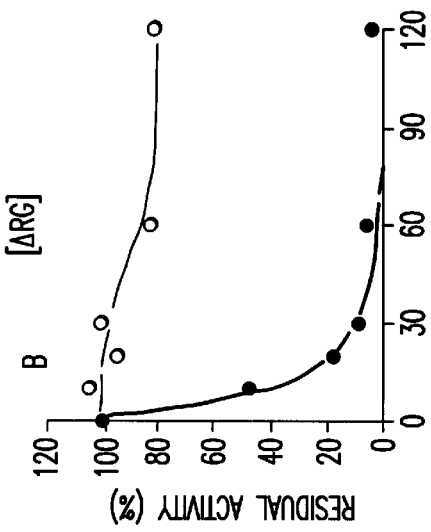
Figure 11C:
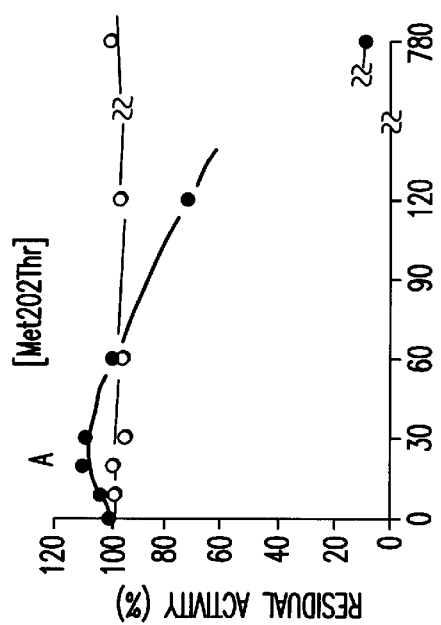
Figure 11D:
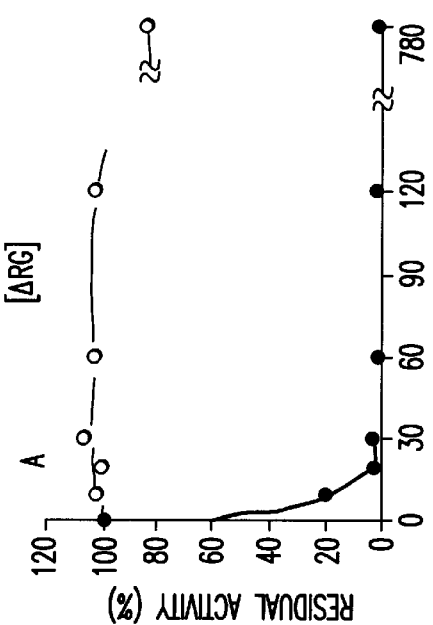
Figure 12:
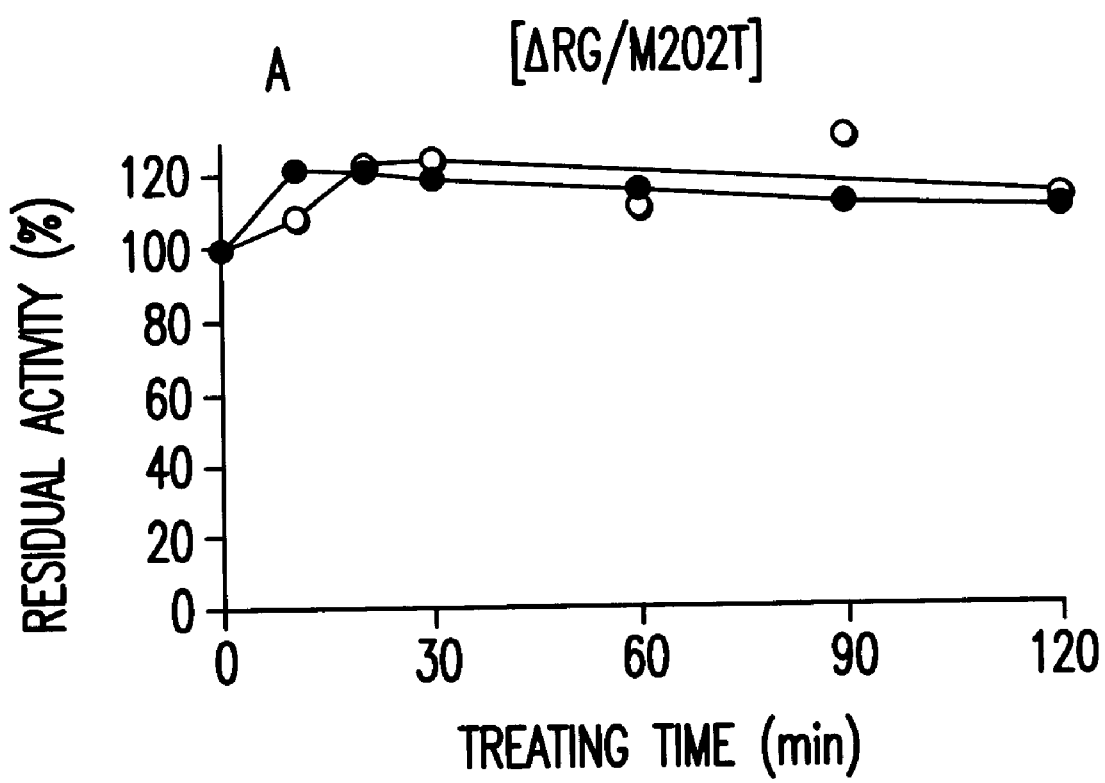
FIG. 12 diagrammatically illustrates the resistance to oxidation with $H_2O_2$ of a mutant α-amylases, ΔRG/Met202Thr, which has been expressed with *Bacillus subtilis* and completely purified. A: residual activities after treated with 500 mM $H_2O_2$ for prescribed periods of time in a 50 mM Tris-HCl buffer (pH: 8.9; in the presence of 0.1 mM $CaCl_2$) under conditions according to the present invention (KAO method). ○: pretreated in the absence of $H_2O_2$ (control), and ●: pretreated with $H_2O_2$ of the prescribed concentration.

(5) The thus-obtained 7 mutant α-amylases having high resistance to oxidation with high-concentration $H_2O_2$ were subjected to mass culture. Each mutant gene was transformed into a *B. subtilis* ISW 1214 strain (LeuA8metB5 hsdM1) in accordance with the protoplast method (Chang & Cohen, Mol. Gen. Genet., 168, 111–115, 1979) (see FIGS. 6 and 7) to conduct culture at 30° C. for 3 days in a liquid medium containing 4% of corn steep liquor; 1% of tryptose;

1.0% of meat extract; 0.1% of potassium primary phosphate; MgSO$_4$, 0.01% of NH$_2$O; 2% of maltose; 0.1% of CaCl$_2$; and 15 μg/ml of tetracycline in a Sakaguchi flask. The resultant culture supernatant was subjected to ammonium sulfate fractionation (to 60% saturation) and dialyzed for 24 hours against a 10 mM Tris-HCl buffer (pH: 7.5; containing 2 mM CaCl$_2$). After the dialysis, the dialyzate was passed through a DEAE-Toyopearl column equilibrated with the same buffer, and the-thus treated solution was then applied into a CM-Toyopearl column equilibrated with the above buffer. As a result the solution was adsorbed on the column, and the intended enzyme was eluted by gradient of NaCl concentration. After this eluate was concentrated on a PM-10 membrane filter (Amicon Co.), the resultant concentrate was dialyzed with the above-described buffer, thereby obtaining a completely purified preparation. All the resultant preparations gave a single band on SDS-electrophoresis (Laemmli, Nature, London, 227, 680–685, 1970), and their molecular weights were all determined to be about 55 KDa.

After the thus-obtained completely purified preparations of the respective mutant α-amylases were separately incubated at 30° C. in a 50 mM Tris buffer (pH: 8.5) containing 2% (588 mM) of H$_2$O$_2$, their residual amylase activities were determined, thereby assaying their resistance to oxidizing agents (KAO method). As a result, the activities of the wild type α-amylase and ΔRG were rapidly decreased as illustrated in FIGS. 8 to 12, while the respective mutant α-amylases exhibited a high residual activity of at least 80% even after incubation for 1 hour. In addition, the respective mutant α-amylases exhibited a high residual amylase activity even under conditions (treated at 30° C. for 30 minutes) that the concentration of H$_2$O$_2$ was increased to 2 M, and it was thus clarified that they gain the extremely high ability to resist oxidizing agents. On the other hand, WO/23873 discloses mutant α-amylases improved in resistance to oxidizing agents. However, these mutant α-amylases are said to exhibit a residual activity of 20 to 43% after treated at 40° C. for 20 minutes in a 50 mM Britton buffer (pH: 9.0) containing 200 mM H$_2$O$_2$ and 0.1 mM CaCl$_2$ (W method). The resistance to oxidizing agents of the mutant α-amylases according to the present invention was assayed by using this W method. As a result, they exhibited a residual activity of at least 80% even after treatment for 1 hour (see FIGS. 8 to 12), and it was thus clarified that they gain extremely high resistance to oxidizing agents compared with the mutant enzymes of WO/23873.

The protein contents of the resultant α-amylase mutants were measured by the above-described method to calculate out their specific activities. As a result, the wild type α-amylase had a specific activity of 4000 to 5500, while Met202Ser had a specific activity of 700 to 750, Met202Thr 2200 to 2400, Met202Val 1100 to 1400, Met202Ala 1350 to 1500, Met202Cys 1450 to 1600, Met202Ile 1600 to 1800, Met202Leu 1600 to 2000, ΔRG 3500 to 4500, ΔRG/Met202Thr 2000 to 2500, NCIB 12512, NCIB 12523 and NCIB 12285 4000 to 4500, and *B. licheniformis* about 1300 (each, unit/mg of protein).

Example 2

The resultant H$_2$O$_2$ oxidation-resistant mutant amylases, Met202Leu and Met202Thr were incubated at 40° C. for 1 hour in a 50 mM Tris-HCl buffer (pH: 8.5) containing a bleaching system of 10 mM TEAD/20 mM NaBO$_4$. The residual amylase activities thereof after the treatment were determined. As a result, the wild type was almost completely inactivated, whereas Met202Leu and Met202Thr retained activities of 77% and 80%, respectively.

Example 3

After granulated Met202Thr (5%, w/v) was incorporated into an ultracompact detergent of A Company, the detergent was stored for 4 weeks in a storeroom controlled at 40 ° C. and 80% relative humidity. The granules were picked up and dissolved in a 50 mM Tris-HCl buffer (pH: 8.5) containing 2 mM CaCl$_2$, and the solution was then centrifuged (12,000×g, 20 minutes). The residual amylase activity of the resultant supernatant was determined. When the specific activities of the wild type and Met202Thr before the treatment were each regarded as 100, the residual activities were 55% for the former and 88% for the latter.

Example 4

Recombinant α-amylases, Met202Leu, Met202Ile, Met202Thr, Met202Val, Met202Cys, Met202Ala and Met202Ser extracellularly produced by *B. subtilis* ISW 1214, the wild type α-amylase, and ΔRG were purified by using the above-described technique. The resultant purified preparations were subjected to SDS-electrophoresis. As a result, they were respectively detected as a single band, and their molecular weights were all determined to be about 55 KDa. The yields thereof were within a range of 40 to 60%.

Referential Example 1

Figure 13A:
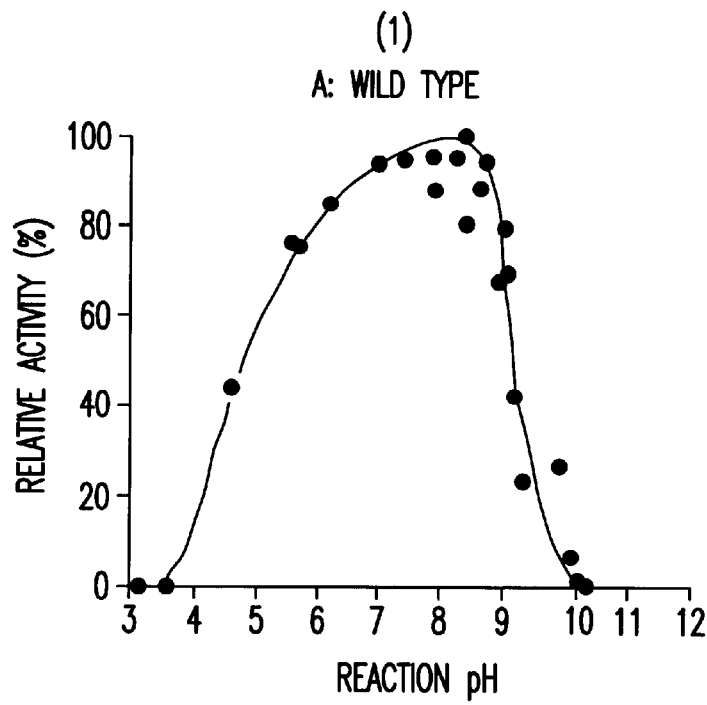
FIG. 13 illustrates a pH-activity curve of a mutant α-amylase by amino acid replacement of methionine at the 202-position, which has been expressed with *Bacillus subtilis* and completely purified. A: wild type, and B: Met202Leu.
Figure 13B:
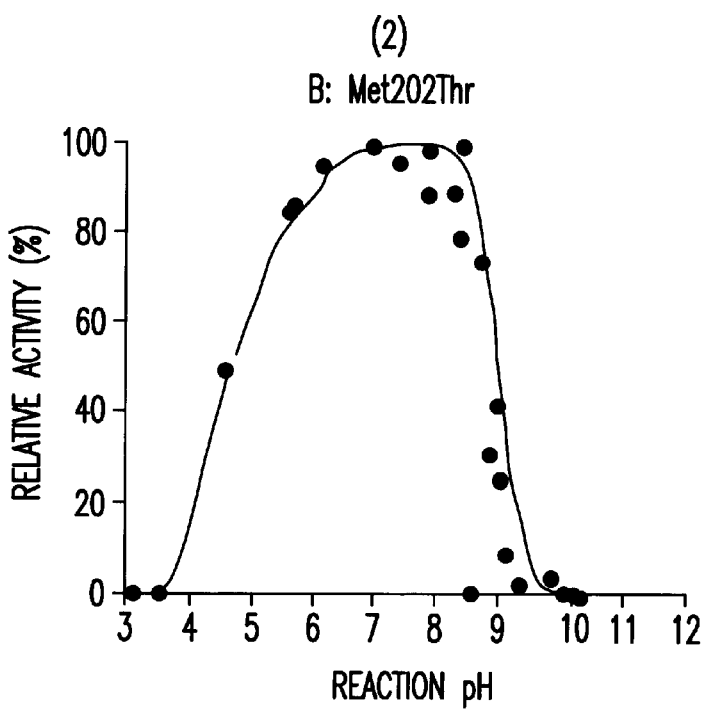
Figure 14A:
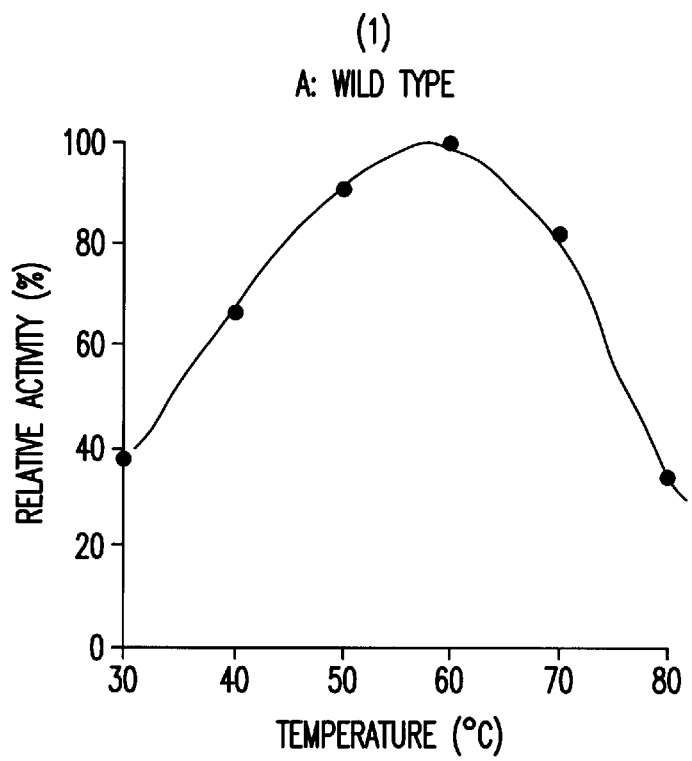
FIG. 14 illustrates a temperature-activity curve of a mutant α-amylase by amino acid replacement of methionine at the 202-position, which has been expressed with *Bacillus subtilis* and completely purified. The activity was determined after conducting a reaction for 5 minutes at a varied temperature in a 50 mM Tris-HCl buffer (pH: 8.5). A: wild type, and B: Met202Leu.
Figure 14B:
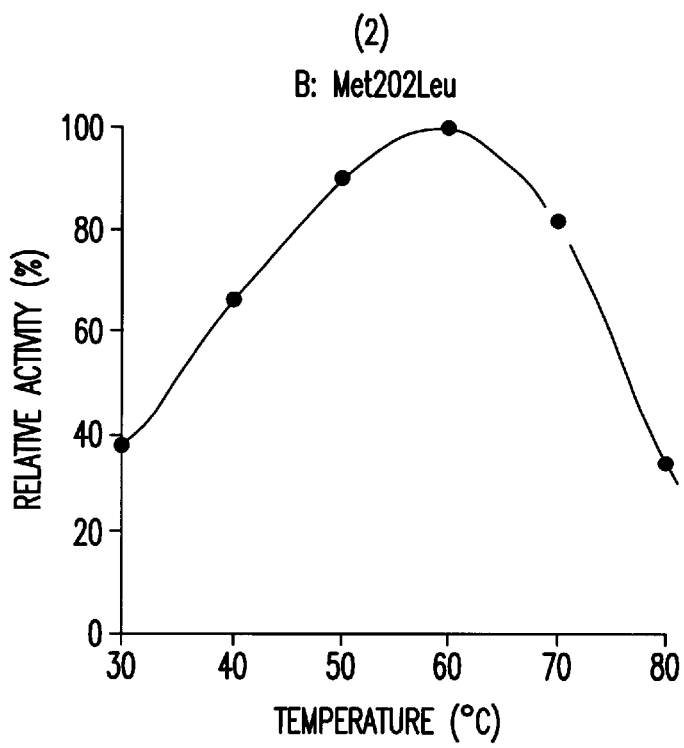

The pH-activity curves of the resultant oxidizing agent-resistant α-amylase mutants were investigated in buffer systems (each 50 mM) with a Britton-Robinson broad buffer combined with various kinds of buffers. As an example thereof, the results of Met202Thr in the respective buffer systems are illustrated in FIG. 13. Even when any buffer system was used, the pH-activity curve showed substantially the same curve as that in the wild type.

Referential Example 2

The temperature-activity curve of the resultant oxidizing agent-resistant α-amylase mutant, Met202Thr was investigated in a 50 mM Tris-HCl buffer (pH: 8.5) (reaction time: 5 minutes). An example of the results thereof is shown in Table 14.

INDUSTRIAL APPLICABILITY

The mutant α-amylases according to the present invention have the optimum pH in an alkaline range, an excellent α-amylase activity, and high and lasting resistance to oxidizing agents, and are hence particularly useful as a component of detergents containing a bleaching agent and an oxidizing agent, and compositions for liquefication and saccharification of starch.

What is claimed is:

1. A mutant α-amylase obtained by introducing a deletion or a replacement of a methionine residue at the 202-position in the amino acid sequence set forth in SEQ ID NO:1, or by introducing a deletion or a replacement of a methionine residue at a position homologous to the 202-position of SEQ ID NO:1 in an amino acid sequence having at least 95.2% homology to SEQ ID NO:1, wherein said deletion or replacement in either said SEQ ID NO:1 or said amino acid sequence having at least 95.2% homology to SEQ ID NO:1 is with an arbitrary amino acid residue, whereby said mutant alpha-amylase has a residual activity of at least 80% after incubation for 1 hour.

2. The mutant α-amylase according to claim 1, wherein said another arbitrary amino acid residue is Thr, Ile, Leu, Ala, Val or Ser.

3. The mutant α-amylase according to claim 1 or 2, wherein an arginine residue at the 181-position and a glycine residue at the 182-position are deleted in said SEQ ID NO:1 or are deleted in said amino acid sequence having 95.2% homology to SEQ ID NO:1.

4. A gene encoding the mutant α-amylase according to claim 1.

5. A detergent composition comprising the mutant α-amylase according to claim 1.

6. The mutant α-amylase according to claim 2, which has an amino acid sequence obtained by making deletion or replacement by another arbitrary amino acid residue of a methionine residue at the 202-position in SEQ ID NO:1, and making deletion of an arginine residue at the 181-position and a glycine residue at the 182-position.

7. A gene encoding the mutant α-amylase according to claim 2.

8. A gene encoding the mutant α-amylase according to claim 3.

9. A detergent composition comprising the mutant α-amylase according to claim 2.

10. A detergent composition comprising the mutant α-amylase according to claim 3.

* * * * *

UNITED STATES PATENT AND TRADEMARK OFFICE
CERTIFICATE OF CORRECTION

PATENT NO.    : 6,486,113 B1                                                Page 1 of 1
DATED         : November 26, 2002
INVENTOR(S)   : Yuji Hatada et al.

It is certified that error appears in the above-identified patent and that said Letters Patent is hereby corrected as shown below:

<u>Title page,</u>
Please change: "[22] PCT Filed: Mar. 31, 1997" to -- [22] PCT Filed: Mar. 31, 1998 --

Signed and Sealed this

Twenty-second Day of July, 2003

JAMES E. ROGAN
*Director of the United States Patent and Trademark Office*

SEQUENCE LISTING

<160> NUMBER OF SEQ ID NOS: 25

<210> SEQ ID NO 1
<211> LENGTH: 485
<212> TYPE: PRT
<213> ORGANISM: Bacillus sp. KSM-AP 1378

<400> SEQUENCE: 1

```
His His Asn Gly Thr Asn Gly Thr Met Met Gln Tyr Phe Glu Trp His
1               5                   10                  15

Leu Pro Asn Asp Gly Asn His Trp Asn Arg Leu Arg Asp Asp Ala Ala
                20                  25                  30

Asn Leu Lys Ser Lys Gly Ile Thr Ala Val Trp Ile Pro Pro Ala Trp
            35                  40                  45

Lys Gly Thr Ser Gln Asn Asp Val Gly Tyr Gly Ala Tyr Asp Leu Tyr
        50                  55                  60

Asp Leu Gly Glu Phe Asn Gln Lys Gly Thr Val Arg Thr Lys Tyr Gly
65                  70                  75                  80

Thr Arg Ser Gln Leu Gln Gly Ala Val Thr Ser Leu Lys Asn Asn Gly
                85                  90                  95

Ile Gln Val Tyr Gly Asp Val Val Met Asn His Lys Gly Gly Ala Asp
            100                 105                 110

Gly Thr Glu Met Val Asn Ala Val Glu Val Asn Arg Ser Asn Arg Asn
        115                 120                 125

Gln Glu Ile Ser Gly Glu Tyr Thr Ile Glu Ala Trp Thr Lys Phe Asp
    130                 135                 140

Phe Pro Gly Arg Gly Asn Thr His Ser Asn Phe Lys Trp Arg Trp Tyr
145                 150                 155                 160

His Phe Asp Gly Thr Asp Trp Asp Gln Ser Arg Gln Leu Gln Asn Lys
                165                 170                 175

Ile Tyr Lys Phe Arg Gly Thr Gly Lys Ala Trp Asp Trp Glu Val Asp
            180                 185                 190

Ile Glu Asn Gly Asn Tyr Asp Tyr Leu Met Tyr Ala Asp Ile Asp Met
        195                 200                 205

Asp His Pro Glu Val Ile Asn Glu Leu Arg Asn Trp Gly Val Trp Tyr
    210                 215                 220

Thr Asn Thr Leu Asn Leu Asp Gly Phe Arg Ile Asp Ala Val Lys His
225                 230                 235                 240

Ile Lys Tyr Ser Tyr Thr Arg Asp Trp Leu Thr His Val Arg Asn Thr
                245                 250                 255

Thr Gly Lys Pro Met Phe Ala Val Ala Glu Phe Trp Lys Asn Asp Leu
            260                 265                 270

Ala Ala Ile Glu Asn Tyr Leu Asn Lys Thr Ser Trp Asn His Ser Val
        275                 280                 285

Phe Asp Val Pro Leu His Tyr Asn Leu Tyr Asn Ala Ser Asn Ser Gly
    290                 295                 300

Gly Tyr Phe Asp Met Arg Asn Ile Leu Asn Gly Ser Val Val Gln Lys
305                 310                 315                 320

His Pro Ile His Ala Val Thr Phe Val Asp Asn His Asp Ser Gln Pro
                325                 330                 335

Gly Glu Ala Leu Glu Ser Phe Val Gln Ser Trp Phe Lys Pro Leu Ala
            340                 345                 350

Tyr Ala Leu Ile Leu Thr Arg Glu Gln Gly Tyr Pro Ser Val Phe Tyr
```

```
                        355                 360                     365
Gly Asp Tyr Tyr Gly Ile Pro Thr His Gly Val Pro Ser Met Lys Ser
        370                 375                 380

Lys Ile Asp Pro Leu Leu Gln Ala Arg Gln Thr Tyr Ala Tyr Gly Thr
385                 390                 395                 400

Gln His Asp Tyr Phe Asp His His Asp Ile Ile Gly Trp Thr Arg Glu
                405                 410                 415

Gly Asp Ser Ser His Pro Asn Ser Gly Leu Ala Thr Ile Met Ser Asp
                420                 425                 430

Gly Pro Gly Gly Asn Lys Trp Met Tyr Val Gly Lys His Lys Ala Gly
            435                 440                 445

Gln Val Trp Arg Asp Ile Thr Gly Asn Arg Ser Gly Thr Val Thr Ile
450                 455                 460

Asn Ala Asp Gly Trp Gly Asn Phe Thr Val Asn Gly Gly Ala Val Ser
465                 470                 475                 480

Val Trp Val Lys Gln
                485

<210> SEQ ID NO 2
<211> LENGTH: 485
<212> TYPE: PRT
<213> ORGANISM: Bacillus sp.

<400> SEQUENCE: 2

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Asp Asp Ala Ala
                20                  25                  30

Asn Leu Lys Ser Lys Gly Ile Thr Ala Val Trp Ile Pro Pro Ala Trp
            35                  40                  45

Lys Gly Thr Ser Gln Asn Asp Val Gly Tyr Gly Ala Tyr Asp Leu Tyr
50                  55                  60

Asp Leu Gly Glu Phe Asn Gln Lys Gly Thr Val Arg Thr Lys Tyr Gly
65                  70                  75                  80

Thr Arg Asn Gln Leu Gln Ala Ala Val Thr Ser Leu Lys Asn Asn Gly
                85                  90                  95

Ile Gln Val Tyr Gly Asp Val Val Met Asn His Lys Gly Gly Ala Asp
                100                 105                 110

Gly Thr Glu Ile Val Asn Ala Val Glu Val Asn Arg Ser Asn Arg Asn
            115                 120                 125

Gln Glu Thr Ser Gly Glu Tyr Ala Ile Glu Ala Trp Thr Lys Phe Asp
130                 135                 140

Phe Pro Gly Arg Gly Asn Asn His Ser Ser Phe Lys Trp Arg Trp Tyr
145                 150                 155                 160

His Phe Asp Gly Thr Asp Trp Asp Gln Ser Arg Gln Leu Gln Asn Lys
                165                 170                 175

Ile Tyr Lys Phe Arg Gly Thr Gly Lys Ala Trp Asp Trp Glu Val Asp
            180                 185                 190

Thr Glu Asn Gly Asn Tyr Asp Tyr Leu Met Tyr Ala Asp Val Asp Met
        195                 200                 205

Asp His Pro Glu Val Ile His Glu Leu Arg Asn Trp Gly Val Trp Tyr
    210                 215                 220

Thr Asn Thr Leu Asn Leu Asp Gly Phe Arg Ile Asp Ala Val Lys His
225                 230                 235                 240
```

-continued

```
Ile Lys Tyr Ser Phe Thr Arg Asp Trp Leu Thr His Val Arg Asn Thr
                245                 250                 255

Thr Gly Lys Pro Met Phe Ala Val Ala Glu Phe Trp Lys Asn Asp Leu
            260                 265                 270

Gly Ala Ile Glu Asn Tyr Leu Asn Lys Thr Ser Trp Asn His Ser Val
        275                 280                 285

Phe Asp Val Pro Leu His Tyr Asn Leu Tyr Asn Ala Ser Asn Ser Gly
    290                 295                 300

Gly Tyr Tyr Asp Met Arg Asn Ile Leu Asn Gly Ser Val Val Gln Lys
305                 310                 315                 320

His Pro Thr His Ala Val Thr Phe Val Asp Asn His Asp Ser Gln Pro
                325                 330                 335

Gly Glu Ala Leu Glu Ser Phe Val Gln Gln Trp Phe Lys Pro Leu Ala
            340                 345                 350

Tyr Ala Leu Val Leu Thr Arg Glu Gln Gly Tyr Pro Ser Val Phe Tyr
        355                 360                 365

Gly Asp Tyr Tyr Gly Ile Pro Thr His Gly Val Pro Ala Met Lys Ser
    370                 375                 380

Lys Ile Asp Pro Leu Leu Gln Ala Arg Gln Thr Phe Ala Tyr Gly Thr
385                 390                 395                 400

Gln His Asp Tyr Phe Asp His His Asp Ile Ile Gly Trp Thr Arg Glu
                405                 410                 415

Gly Asn Ser Ser His Pro Asn Ser Gly Leu Ala Thr Ile Met Ser Asp
            420                 425                 430

Gly Pro Gly Gly Asn Lys Trp Met Tyr Val Gly Lys Asn Lys Ala Gly
        435                 440                 445

Gln Val Trp Arg Asp Ile Thr Gly Asn Arg Thr Gly Thr Val Thr Ile
    450                 455                 460

Asn Ala Asp Gly Trp Gly Asn Phe Ser Val Asn Gly Gly Ser Val Ser
465                 470                 475                 480

Val Trp Val Lys Gln
                485

<210> SEQ ID NO 3
<211> LENGTH: 485
<212> TYPE: PRT
<213> ORGANISM: Bacillus sp.

<400> SEQUENCE: 3

His His Asn Gly Thr Asn Gly Thr Met Met Gln Tyr Phe Glu Trp His
1               5                   10                  15

Leu Pro Asn Asp Gly Asn His Trp Asn Arg Leu Arg Asp Asp Ala Ser
                20                  25                  30

Asn Leu Arg Asn Arg Gly Ile Thr Ala Ile Trp Ile Pro Pro Ala Trp
            35                  40                  45

Lys Gly Thr Ser Gln Asn Asp Val Gly Tyr Gly Ala Tyr Asp Leu Tyr
        50                  55                  60

Asp Leu Gly Glu Phe Asn Gln Lys Gly Thr Val Arg Thr Lys Tyr Gly
65                  70                  75                  80

Thr Arg Ser Gln Leu Glu Ser Ala Ile His Ala Leu Lys Asn Asn Gly
                85                  90                  95

Val Gln Val Tyr Gly Asp Val Val Met Asn His Lys Gly Gly Ala Asp
            100                 105                 110

Ala Thr Glu Asn Val Leu Ala Val Glu Val Asn Pro Asn Asn Arg Asn
        115                 120                 125
```

```
Gln Glu Ile Ser Gly Asp Tyr Thr Ile Glu Ala Trp Thr Lys Phe Asp
    130                 135                 140
Phe Pro Gly Arg Gly Asn Thr Tyr Ser Asp Phe Lys Trp Arg Trp Tyr
145                 150                 155                 160
His Phe Asp Gly Val Asp Trp Asp Gln Ser Arg Gln Phe Gln Asn Arg
                165                 170                 175
Ile Tyr Lys Phe Arg Gly Asp Gly Lys Ala Trp Asp Trp Glu Val Asp
            180                 185                 190
Ser Glu Asn Gly Asn Tyr Asp Tyr Leu Met Tyr Ala Asp Val Asp Met
        195                 200                 205
Asp His Pro Glu Val Val Asn Glu Leu Arg Arg Trp Gly Glu Trp Tyr
    210                 215                 220
Thr Asn Thr Leu Asn Leu Asp Gly Phe Arg Ile Asp Ala Val Lys His
225                 230                 235                 240
Ile Lys Tyr Ser Phe Thr Arg Asp Trp Leu Thr His Val Arg Asn Ala
                245                 250                 255
Thr Gly Lys Glu Met Phe Ala Val Ala Glu Phe Trp Lys Asn Asp Leu
            260                 265                 270
Gly Ala Leu Glu Asn Tyr Leu Asn Lys Thr Asn Trp Asn His Ser Val
        275                 280                 285
Phe Asp Val Pro Leu His Tyr Asn Leu Tyr Asn Ala Ser Asn Ser Gly
    290                 295                 300
Gly Asn Tyr Asp Met Ala Lys Leu Leu Asn Gly Thr Val Val Gln Lys
305                 310                 315                 320
His Pro Met His Ala Val Thr Phe Val Asp Asn His Asp Ser Gln Pro
                325                 330                 335
Gly Glu Ser Leu Glu Ser Phe Val Gln Glu Trp Phe Lys Pro Leu Ala
            340                 345                 350
Tyr Ala Leu Ile Leu Thr Arg Glu Gln Gly Tyr Pro Ser Val Phe Tyr
        355                 360                 365
Gly Asp Tyr Tyr Gly Ile Pro Thr His Ser Val Pro Ala Met Lys Ala
    370                 375                 380
Lys Ile Asp Pro Ile Leu Glu Ala Arg Gln Asn Phe Ala Tyr Gly Thr
385                 390                 395                 400
Gln His Asp Tyr Phe Asp His His Asn Ile Ile Gly Trp Thr Arg Glu
                405                 410                 415
Gly Asn Thr Thr His Pro Asn Ser Gly Leu Ala Thr Ile Met Ser Asp
            420                 425                 430
Gly Pro Gly Gly Glu Lys Trp Met Tyr Val Gly Gln Asn Lys Ala Gly
        435                 440                 445
Gln Val Trp His Asp Ile Thr Gly Asn Lys Pro Gly Thr Val Thr Ile
    450                 455                 460
Asn Ala Asp Gly Trp Ala Asn Phe Ser Val Asn Gly Gly Ser Val Ser
465                 470                 475                 480
Ile Trp Val Lys Arg
                485

<210> SEQ ID NO 4
<211> LENGTH: 486
<212> TYPE: PRT
<213> ORGANISM: Bacillus sp.

<400> SEQUENCE: 4

His His Asn Gly Thr Asn Gly Thr Met Met Gln Tyr Phe Glu Trp Tyr
```

```
1               5                   10                  15

Leu Pro Asn Asp Gly Asn His Trp Asn Arg Leu Arg Asp Ala Ala
            20                  25              30

Asn Leu Lys Ser Lys Gly Ile Thr Ala Val Trp Ile Pro Pro Ala Trp
            35                  40                  45

Lys Gly Thr Ser Gln Asn Asp Val Gly Tyr Gly Ala Tyr Asp Leu Tyr
    50                  55                  60

Asp Leu Gly Glu Phe Asn Asn Gln Lys Gly Thr Val Arg Thr Lys Tyr
65                  70                  75                  80

Gly Thr Arg Asn Gln Leu Gln Ala Ala Val Thr Ser Leu Lys Asn Asn
                85                  90                  95

Gly Ile Gln Val Tyr Gly Asp Val Val Met Asn His Lys Gly Gly Ala
                100                 105             110

Asp Gly Thr Glu Ile Val Asn Ala Val Glu Val Asn Arg Ser Asn Arg
            115                 120                 125

Asn Gln Glu Thr Ser Gly Glu Tyr Ala Ile Glu Ala Trp Thr Lys Phe
    130                 135                 140

Asp Phe Pro Gly Arg Gly Asn Asn His Ser Ser Phe Lys Trp Arg Trp
145                 150                 155                 160

Tyr His Phe Asp Gly Thr Asp Trp Asp Gln Ser Arg Gln Leu Gln Asn
                165                 170                 175

Lys Ile Tyr Lys Phe Arg Gly Thr Gly Lys Ala Trp Asp Trp Glu Val
                180                 185                 190

Asp Thr Glu Asn Gly Asn Tyr Asp Tyr Leu Met Tyr Ala Asp Val Asp
                195                 200                 205

Met Asp His Pro Glu Val Ile His Glu Leu Arg Asn Trp Gly Val Trp
    210                 215                 220

Tyr Thr Asn Thr Leu Asn Leu Asp Gly Phe Arg Ile Asp Ala Val Lys
225                 230                 235                 240

His Ile Lys Tyr Ser Phe Thr Arg Asp Trp Leu Thr His Val Arg Asn
                245                 250                 255

Thr Thr Gly Lys Pro Met Phe Ala Val Ala Glu Phe Trp Lys Asn Asp
                260                 265                 270

Leu Gly Ala Ile Glu Asn Tyr Leu Asn Lys Thr Ser Trp Asn His Ser
                275                 280                 285

Ala Phe Asp Val Pro Leu His Tyr Asn Leu Tyr Asn Ala Ser Asn Ser
    290                 295                 300

Gly Gly Tyr Tyr Asp Met Arg Asn Ile Leu Asn Gly Ser Val Val Gln
305                 310                 315                 320

Lys His Pro Thr His Ala Val Thr Phe Val Asp Asn His Asp Ser Gln
                325                 330                 335

Pro Gly Glu Ala Leu Glu Ser Phe Val Gln Gln Trp Phe Lys Pro Leu
            340                 345                 350

Ala Tyr Ala Leu Val Leu Thr Arg Glu Gln Gly Tyr Pro Ser Val Phe
    355                 360                 365

Tyr Gly Asp Tyr Tyr Gly Ile Pro Thr His Gly Val Pro Ala Met Lys
370                 375                 380

Ser Lys Ile Asp Pro Leu Leu Gln Ala Arg Gln Thr Phe Ala Tyr Gly
385                 390                 395                 400

Thr Gln His Asp Tyr Phe Asp His His Asp Ile Ile Gly Trp Thr Arg
                405                 410                 415

Glu Gly Asn Ser Ser His Pro Asn Ser Gly Leu Ala Thr Ile Met Ser
                420                 425                 430
```

-continued

```
Asp Gly Pro Gly Gly Asn Lys Trp Met Tyr Val Gly Lys Asn Lys Ala
        435                 440                 445

Gly Gln Val Trp Arg Asp Ile Thr Gly Asn Arg Thr Gly Thr Val Thr
    450                 455                 460

Ile Asn Ala Asp Gly Trp Gly Asn Phe Ser Val Asn Gly Gly Ser Val
465                 470                 475                 480

Ser Val Trp Val Lys Gln
                485

<210> SEQ ID NO 5
<211> LENGTH: 485
<212> TYPE: PRT
<213> ORGANISM: Bacillus sp. #707

<400> SEQUENCE: 5

His His Asn Gly Thr Asn Gly Thr Met Met Gln Tyr Phe Glu Trp Tyr
1               5                  10                  15

Leu Pro Asn Asp Gly Asn His Trp Asn Arg Leu Asn Ser Asp Ala Ser
            20                  25                  30

Asn Leu Lys Ser Lys Gly Ile Thr Ala Val Trp Ile Pro Pro Ala Trp
        35                  40                  45

Lys Gly Ala Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Arg Ser Gln Leu Gln Ala Ala Val Thr Ser Leu Lys Asn Asn Gly
                85                  90                  95

Ile Gln Val Tyr Gly Asp Val Val Met Asn His Lys Gly Gly Ala Asp
            100                 105                 110

Ala Thr Glu Met Val Arg Ala Val Glu Val Asn Pro Asn Asn Arg Asn
        115                 120                 125

Gln Glu Val Thr Gly Glu Tyr Thr Ile Glu Ala Trp Thr Arg Phe Asp
    130                 135                 140

Phe Pro Gly Arg Gly Asn Thr His Ser Ser Phe Lys Trp Arg Trp Tyr
145                 150                 155                 160

His Phe Asp Gly Val Asp Trp Asp Gln Ser Arg Arg Leu Asn Asn Arg
                165                 170                 175

Ile Tyr Lys Phe Arg Gly His Gly Lys Ala Trp Asp Trp Glu Val Asp
            180                 185                 190

Thr Glu Asn Gly Asn Tyr Asp Tyr Leu Met Tyr Ala Asp Ile Asp Met
        195                 200                 205

Asp His Pro Glu Val Val Asn Glu Leu Arg Asn Trp Gly Val Trp Tyr
    210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Ile Asn His Val Arg Ser Ala
                245                 250                 255

Thr Gly Lys Asn Met Phe Ala Val Ala Glu Phe Trp Lys Asn Asp Leu
            260                 265                 270

Gly Ala Ile Glu Asn Tyr Leu Gln Lys Thr Asn Trp Asn His Ser Val
        275                 280                 285

Phe Asp Val Pro Leu His Tyr Asn Leu Tyr Asn Ala Ser Lys Ser Gly
    290                 295                 300

Gly Asn Tyr Asp Met Arg Asn Ile Phe Asn Gly Thr Val Val Gln Arg
```

```
                305                 310                 315                 320
His Pro Ser His Ala Thr Phe Val Asp Asn His Asp Ser Gln Pro
            325                 330                 335
Glu Glu Ala Leu Glu Ser Phe Val Glu Glu Trp Phe Lys Pro Leu Ala
            340                 345                 350
Tyr Ala Leu Thr Leu Thr Arg Glu Gln Gly Tyr Pro Ser Val Phe Tyr
            355                 360                 365
Gly Asp Tyr Tyr Gly Ile Pro Thr His Gly Val Pro Ala Met Arg Ser
            370                 375                 380
Lys Ile Asp Pro Ile Leu Glu Ala Arg Gln Lys Tyr Ala Tyr Gly Lys
385                 390                 395                 400
Gln Asn Asp Tyr Leu Asp His His Asn Ile Ile Gly Trp Thr Arg Glu
            405                 410                 415
Gly Asn Thr Ala His Pro Asn Ser Gly Leu Ala Thr Ile Met Ser Asp
            420                 425                 430
Gly Ala Gly Gly Ser Lys Trp Met Phe Val Gly Arg Asn Lys Ala Gly
            435                 440                 445
Gln Val Trp Ser Asp Ile Thr Gly Asn Arg Thr Gly Thr Val Thr Ile
            450                 455                 460
Asn Ala Asp Gly Trp Gly Asn Phe Ser Val Asn Gly Gly Ser Val Ser
465                 470                 475                 480
Ile Trp Val Asn Lys
            485

<210> SEQ ID NO 6
<211> LENGTH: 483
<212> TYPE: PRT
<213> ORGANISM: B. amyloliquefaciens

<400> SEQUENCE: 6

Val Asn Gly Thr Leu Met Gln Tyr Phe Glu Trp Tyr Thr Pro Asn Asp
1               5                   10                  15
Gly Gln His Trp Lys Arg Leu Gln Asn Asp Ala Glu His Leu Ser Asp
            20                  25                  30
Ile Gly Ile Thr Ala Val Trp Ile Pro Pro Ala Tyr Lys Gly Leu Ser
            35                  40                  45
Gln Ser Asp Asn Gly Tyr Gly Pro Tyr Asp Leu Tyr Asp Leu Gly Glu
        50                  55                  60
Phe Gln Gln Lys Gly Thr Val Arg Thr Lys Tyr Gly Thr Lys Ser Glu
65                  70                  75                  80
Leu Gln Asp Ala Ile Gly Ser Leu His Ser Arg Asn Val Gln Val Tyr
                85                  90                  95
Gly Asp Val Val Leu Asn His Lys Ala Gly Ala Asp Ala Thr Glu Asp
            100                 105                 110
Val Thr Ala Val Glu Val Asn Pro Ala Asn Arg Asn Gln Glu Thr Ser
            115                 120                 125
Glu Glu Tyr Gln Ile Lys Ala Trp Thr Asp Phe Arg Phe Pro Gly Arg
        130                 135                 140
Gly Asn Thr Tyr Ser Asp Phe Lys Trp His Trp Tyr His Phe Asp Gly
145                 150                 155                 160
Ala Asp Trp Asp Glu Ser Arg Lys Ile Ser Arg Ile Phe Lys Phe Arg
                165                 170                 175
Gly Glu Gly Lys Ala Trp Asp Trp Glu Val Ser Ser Glu Asn Gly Asn
            180                 185                 190
```

```
Tyr Asp Tyr Leu Met Tyr Ala Asp Val Asp Tyr Asp His Pro Asp Val
            195                 200                 205

Val Ala Glu Thr Lys Lys Trp Gly Ile Trp Tyr Ala Asn Glu Leu Ser
    210                 215                 220

Leu Asp Gly Phe Arg Ile Asp Ala Ala Lys His Ile Lys Phe Ser Phe
225                 230                 235                 240

Leu Arg Asp Trp Val Gln Ala Val Arg Gln Ala Thr Gly Lys Glu Met
                245                 250                 255

Phe Thr Val Ala Glu Tyr Trp Gln Asn Asn Ala Gly Lys Leu Glu Asn
            260                 265                 270

Tyr Leu Asn Lys Thr Ser Phe Asn Gln Ser Val Phe Asp Val Pro Leu
        275                 280                 285

His Phe Asn Leu Gln Ala Ala Ser Ser Gln Gly Gly Gly Tyr Asp Met
    290                 295                 300

Arg Arg Leu Leu Asp Gly Thr Val Val Ser Arg His Pro Glu Lys Ala
305                 310                 315                 320

Val Thr Phe Val Glu Asn His Asp Thr Gln Pro Gly Gln Ser Leu Glu
                325                 330                 335

Ser Thr Val Gln Thr Trp Phe Lys Pro Leu Ala Tyr Ala Phe Ile Leu
            340                 345                 350

Thr Arg Glu Ser Gly Tyr Pro Gln Val Phe Tyr Gly Asp Met Tyr Gly
        355                 360                 365

Thr Lys Gly Thr Ser Pro Lys Glu Ile Pro Ser Leu Lys Asp Asn Ile
    370                 375                 380

Glu Pro Ile Leu Lys Ala Arg Lys Glu Tyr Ala Tyr Gly Pro Gln His
385                 390                 395                 400

Asp Tyr Ile Asp His Pro Asp Val Ile Gly Trp Thr Arg Glu Gly Asp
                405                 410                 415

Ser Ser Ala Ala Lys Ser Gly Leu Ala Ala Leu Ile Thr Asp Gly Pro
            420                 425                 430

Gly Gly Ser Lys Arg Met Tyr Ala Gly Leu Lys Asn Ala Gly Glu Thr
        435                 440                 445

Trp Tyr Asp Ile Thr Gly Asn Arg Ser Asp Thr Val Lys Ile Gly Ser
    450                 455                 460

Asp Gly Trp Gly Glu Phe His Val Asn Asp Gly Ser Val Ser Ile Tyr
465                 470                 475                 480

Val Gln Lys

<210> SEQ ID NO 7
<211> LENGTH: 515
<212> TYPE: PRT
<213> ORGANISM: B. stearothermophilus

<400> SEQUENCE: 7

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
    50                  55                  60

Leu Gly Glu Phe Asn Gln Lys Gly Thr Val Arg Thr Lys Tyr Gly Thr
65                  70                  75                  80
```

-continued

```
Lys Ala Gln Tyr Leu Gln Ala Ile Gln Ala His Ala Ala Gly Met
                 85                  90                  95

Gln Val Tyr Ala Asp Val Val Phe Asp His Lys Gly Ala Asp Gly
                100                 105                 110

Thr Glu Trp Val Asp Ala Val Glu Val Asn Pro Ser Asp Arg Asn Gln
                115                 120                 125

Glu Ile Ser Gly Thr Tyr Gln Ile Gln Ala Trp Thr Lys Phe Asp Phe
130                 135                 140

Asn Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Ile Gly Lys Ala Trp Asp Trp Glu Val Asp Thr Glu
                180                 185                 190

Asn Gly Asn Tyr Asp Tyr Leu Met Tyr Ala Asp Leu Asp Met Asp His
                195                 200                 205

Pro Glu Val Val Thr Glu Leu Lys Asn Trp Gly Lys Trp Tyr Val Asn
        210                 215                 220

Thr Thr Asn Ile Asp Gly Phe Arg Leu Asp Ala Val Lys His Ile Lys
225                 230                 235                 240

Phe Ser Phe Phe Pro Asp Trp Leu Ser Tyr Val Arg Ser Gln Thr Gly
                245                 250                 255

Lys Pro Leu Phe Thr Val Gly Glu Tyr Trp Ser Tyr Asp Ile Asn Lys
                260                 265                 270

Leu His Asn Tyr Ile Thr Lys Thr Asn Gly Thr Met Ser Leu Phe Asp
                275                 280                 285

Ala Pro Leu His Asn Lys Phe Tyr Thr Ala Ser Lys Ser Gly Gly Ala
        290                 295                 300

Phe Asp Met Ser Thr Leu Met Asn Asn Thr Leu Met Lys Asp Gln Pro
305                 310                 315                 320

Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
                340                 345                 350

Phe Ile Leu Thr Arg Gln Glu Gly Tyr Pro Cys Val Phe Tyr Gly Asp
                355                 360                 365

Tyr Tyr Gly Ile Pro Gln Tyr Asn Ile Pro Ser Leu Lys Ser Lys Ile
370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
                405                 410                 415

Thr Glu Lys Pro Gly Ser Gly Leu Ala Ala Leu Ile Thr Asp Gly Pro
                420                 425                 430

Gly Gly Ser Lys Trp Met Tyr Val Gly Lys Gln His Ala Gly Lys Val
                435                 440                 445

Phe Tyr Asp Leu Thr Gly Asn Arg Ser Asp Thr Val Thr Ile Asn Ser
        450                 455                 460

Asp Gly Trp Gly Glu Phe Lys Val Asn Gly Gly Ser Val Ser Val Trp
465                 470                 475                 480

Val Pro Arg Lys Thr Thr Val Ser Thr Ile Ala Trp Pro Ile Thr Thr
                485                 490                 495

Arg Pro Trp Thr Gly Glu Phe Val Arg Trp Thr Glu Pro Arg Leu Val
```

```
                      500             505             510
Ala Trp Pro
        515

<210> SEQ ID NO 8
<211> LENGTH: 483
<212> TYPE: PRT
<213> ORGANISM: B. licheniformis

<400> SEQUENCE: 8

Ala Asn Leu Asn Gly Thr Leu Met Gln Tyr Phe Glu Trp Tyr Met Pro
1               5                   10                  15

Asn Asp Gly Gln His Trp Lys Arg Leu Gln Asn Asp Ser Ala Tyr Leu
            20                  25                  30

Ala Glu His Gly Ile Thr Ala Val Trp Ile Pro Pro Ala Tyr Lys Gly
        35                  40                  45

Thr Ser Gln Ala Asp Val Gly Tyr Gly Ala Tyr Asp Leu Tyr Asp Leu
    50                  55                  60

Gly Glu Phe His Gln Lys Gly Thr Val Arg Thr Lys Tyr Gly Thr Lys
65                  70                  75                  80

Gly Glu Leu Gln Ser Ala Ile Lys Ser Leu His Ser Arg Asp Ile Asn
                85                  90                  95

Val Tyr Gly Asp Val Val Ile Asn His Lys Gly Gly Ala Asp Ala Thr
            100                 105                 110

Glu Asp Val Thr Ala Val Glu Val Asp Pro Ala Asp Arg Asn Arg Val
        115                 120                 125

Ile Ser Gly Glu His Arg Ile Lys Ala Trp Thr His Phe His Phe Pro
    130                 135                 140

Gly Arg Gly Ser Thr Tyr Ser Asp Phe Lys Trp His Trp Tyr His Phe
145                 150                 155                 160

Asp Gly Thr Asp Trp Asp Glu Ser Arg Lys Leu Asn Arg Ile Tyr Lys
                165                 170                 175

Phe Gln Gly Lys Ala Trp Asp Trp Glu Val Ser Asn Glu Asn Gly Asn
            180                 185                 190

Tyr Asp Tyr Leu Met Tyr Ala Asp Ile Asp Tyr Asp His Pro Asp Val
        195                 200                 205

Ala Ala Glu Ile Lys Arg Trp Gly Thr Trp Tyr Ala Asn Glu Leu Gln
    210                 215                 220

Leu Asp Gly Phe Arg Leu Asp Ala Val Lys His Ile Lys Phe Ser Phe
225                 230                 235                 240

Leu Arg Asp Trp Val Asn His Val Arg Glu Lys Thr Gly Lys Glu Met
                245                 250                 255

Phe Thr Val Ala Glu Tyr Trp Gln Asn Asp Leu Gly Ala Leu Glu Asn
            260                 265                 270

Tyr Leu Asn Lys Thr Asn Phe Asn His Ser Val Phe Asp Val Pro Leu
        275                 280                 285

His Tyr Gln Phe His Ala Ala Ser Thr Gln Gly Gly Gly Tyr Asp Met
    290                 295                 300

Arg Lys Leu Leu Asn Ser Thr Val Val Ser Lys His Pro Leu Lys Ala
305                 310                 315                 320

Val Thr Phe Val Asp Asn His Asp Thr Gln Pro Gly Gln Ser Leu Glu
                325                 330                 335

Ser Thr Val Gln Thr Trp Phe Lys Pro Leu Ala Tyr Ala Phe Ile Leu
            340                 345                 350
```

```
Thr Arg Glu Ser Gly Tyr Pro Gln Val Phe Tyr Gly Asp Met Tyr Gly
            355                 360                 365

Thr Lys Gly Asp Ser Gln Arg Glu Ile Pro Ala Leu Lys His Lys Ile
    370                 375                 380

Glu Pro Ile Leu Lys Ala Arg Lys Gln Tyr Ala Tyr Gly Ala Gln His
385                 390                 395                 400

Asp Tyr Phe Asp His His Asp Ile Val Gly Trp Thr Arg Glu Gly Asp
                405                 410                 415

Ser Ser Val Ala Asn Ser Gly Leu Ala Ala Leu Ile Thr Asp Gly Pro
            420                 425                 430

Gly Gly Ala Lys Arg Met Tyr Val Gly Arg Gln Asn Ala Gly Glu Thr
        435                 440                 445

Trp His Asp Ile Thr Gly Asn Arg Ser Glu Pro Val Val Ile Asn Ser
    450                 455                 460

Glu Gly Trp Gly Glu Phe His Val Asn Gly Gly Ser Val Ser Ile Tyr
465                 470                 475                 480

Val Gln Arg

<210> SEQ ID NO 9
<211> LENGTH: 24
<212> TYPE: DNA
<213> ORGANISM: Artificial
<220> FEATURE:
<223> OTHER INFORMATION: Primer targeted to the Bacillus sp.
      alpha-amylase gene

<400> SEQUENCE: 9
taccttctgt atgcagacat tgat                                        24

<210> SEQ ID NO 10
<211> LENGTH: 24
<212> TYPE: DNA
<213> ORGANISM: Artificial
<220> FEATURE:
<223> OTHER INFORMATION: Met202Ala primer targeted to the Bacillus sp.
      alpha-amylase gene

<400> SEQUENCE: 10
taccttgcat atgcagacat tgat                                        24

<210> SEQ ID NO 11
<211> LENGTH: 24
<212> TYPE: DNA
<213> ORGANISM: Artificial
<220> FEATURE:
<223> OTHER INFORMATION: Met202Ile primer targeted to the Bacillus sp.
      alpha-amylase gene

<400> SEQUENCE: 11
taccttatct atgcagacat tgat                                        24

<210> SEQ ID NO 12
<211> LENGTH: 24
<212> TYPE: DNA
<213> ORGANISM: Artificial
<220> FEATURE:
<223> OTHER INFORMATION: Met202Ser primer targeted to the Bacillus sp.
      alpha-amylase gene

<400> SEQUENCE: 12
tacctttcat atgcagacat tgat                                        24
```

```
<210> SEQ ID NO 13
<211> LENGTH: 24
<212> TYPE: DNA
<213> ORGANISM: Artificial
<220> FEATURE:
<223> OTHER INFORMATION: Met202Thr primer targeted to the Bacillus sp.
      alpha-amylase gene

<400> SEQUENCE: 13
taccttacat atgcagacat tgat                                              24

<210> SEQ ID NO 14
<211> LENGTH: 24
<212> TYPE: DNA
<213> ORGANISM: Artificial
<220> FEATURE:
<223> OTHER INFORMATION: Met202Val primer targeted to the Bacillus sp.
      alpha-amylase gene

<400> SEQUENCE: 14
taccttgtgt atgcagacat tgat                                              24

<210> SEQ ID NO 15
<211> LENGTH: 24
<212> TYPE: DNA
<213> ORGANISM: Artificial
<220> FEATURE:
<223> OTHER INFORMATION: Met202Cys primer targeted to the Bacillus sp.
      alpha-amylase gene

<400> SEQUENCE: 15
tacctttgct atgcagacat tgat                                              24

<210> SEQ ID NO 16
<211> LENGTH: 27
<212> TYPE: DNA
<213> ORGANISM: Artificial
<220> FEATURE:
<223> OTHER INFORMATION: Met9Leu primer targeted to the Bacillus sp.
      alpha-amylase gene

<400> SEQUENCE: 16
acgaatggga ccctgatgca gtatttt                                           27

<210> SEQ ID NO 17
<211> LENGTH: 27
<212> TYPE: DNA
<213> ORGANISM: Artificial
<220> FEATURE:
<223> OTHER INFORMATION: Met105Ile primer targeted to the Bacillus sp.
      alpha-amylase gene

<400> SEQUENCE: 17
ggggatgtcg tgatcaatca taaaggt                                           27

<210> SEQ ID NO 18
<211> LENGTH: 27
<212> TYPE: DNA
<213> ORGANISM: Artificial
<220> FEATURE:
<223> OTHER INFORMATION: Met116Asp primer targeted to the Bacillus sp.
      alpha-amylase gene

<400> SEQUENCE: 18
gacgggacag aggacgtaaa tgcggtg                                           27

<210> SEQ ID NO 19
```

```
<211> LENGTH: 27
<212> TYPE: DNA
<213> ORGANISM: Artificial
<220> FEATURE:
<223> OTHER INFORMATION: Met382Leu primer targeted to the Bacillus sp.
      alpha-amylase gene

<400> SEQUENCE: 19
ggtgttcctt cgctgaaatc taaaatt                                           27

<210> SEQ ID NO 20
<211> LENGTH: 27
<212> TYPE: DNA
<213> ORGANISM: Artificial
<220> FEATURE:
<223> OTHER INFORMATION: Met430Ile primer targeted to the Bacillus sp.
      alpha-amylase gene

<400> SEQUENCE: 20
cttgcaacta ttatctccga tgggcca                                           27

<210> SEQ ID NO 21
<211> LENGTH: 27
<212> TYPE: DNA
<213> ORGANISM: Artificial
<220> FEATURE:
<223> OTHER INFORMATION: Met208Tyr primer targeted to the Bacillus sp.
      alpha-amylase gene

<400> SEQUENCE: 21
gcagacattg attatgatca tccagaa                                           27

<210> SEQ ID NO 22
<211> LENGTH: 42
<212> TYPE: DNA
<213> ORGANISM: Artificial
<220> FEATURE:
<223> OTHER INFORMATION: Primer targeted to the Bacillus sp.
      alpha-amylase gene
<221> NAME/KEY: misc_feature
<222> LOCATION: (16)..(21)
<223> OTHER INFORMATION: Deleted bases

<400> SEQUENCE: 22
aaaatatata aattcagagg taccggaaag gcatgggact gg                          42

<210> SEQ ID NO 23
<211> LENGTH: 26
<212> TYPE: DNA
<213> ORGANISM: Artificial
<220> FEATURE:
<223> OTHER INFORMATION: Primer targeted to the Bacillus sp.
      alpha-amylase gene

<400> SEQUENCE: 23
agtacttacc attttagagt caaaag                                            26

<210> SEQ ID NO 24
<211> LENGTH: 26
<212> TYPE: DNA
<213> ORGANISM: Artificial
<220> FEATURE:
<223> OTHER INFORMATION: Primer targeted to the Bacillus sp.
      alpha-amylase gene

<400> SEQUENCE: 24
aagcttccaa tttatattgg gtgtat                                            26
```

```
<210> SEQ ID NO 25
<211> LENGTH: 30
<212> TYPE: DNA
<213> ORGANISM: Artificial
<220> FEATURE:
<223> OTHER INFORMATION: Primer targeted to the Bacillus sp.
      alpha-amylase gene

<400> SEQUENCE: 25
gagtcgacca gcacaagccc atcataatgg                                    30
```